(12) United States Patent
Rees

(10) Patent No.: US 7,973,299 B2
(45) Date of Patent: Jul. 5, 2011

(54) SYSTEM AND METHOD FOR PROVIDING A SUSPENDED PERSONAL RADIATION PROTECTION SYSTEM

(76) Inventor: Chet R. Rees, Dallas, TX (US)

( * ) Notice: Subject to any disclaimer, the term of this patent is extended or adjusted under 35 U.S.C. 154(b) by 356 days.

(21) Appl. No.: 12/099,077

(22) Filed: Apr. 7, 2008

(65) Prior Publication Data
US 2009/0184269 A1    Jul. 23, 2009

Related U.S. Application Data

(60) Provisional application No. 61/022,174, filed on Jan. 18, 2008.

(51) Int. Cl.
*G21F 3/02* (2006.01)
(52) U.S. Cl. .................... 250/516.1; 250/519.1
(58) Field of Classification Search ........... 250/516.1, 250/519.1, 515.1
See application file for complete search history.

(56) References Cited

U.S. PATENT DOCUMENTS

| | | | |
|---|---|---|---|
| 1,636,419 A | 7/1927 | Hollander | |
| 2,718,598 A | 9/1955 | Graf | 250/58 |
| 2,794,128 A | 5/1957 | Shasky | 250/108 |
| 3,308,297 A | 3/1967 | Mansker | 250/108 |
| 4,254,341 A | 3/1981 | Herr et al. | 250/519 |
| 4,286,170 A | 8/1981 | Moti | 250/515.1 |
| 4,581,538 A | 4/1986 | Lenhart | 250/519.1 |
| 4,654,188 A | 3/1987 | Hankinson | 376/260 |
| D300,945 S | 5/1989 | Fleming et al. | D24/2 |
| 4,932,078 A | 6/1990 | Jones et al. | |
| 5,006,718 A | 4/1991 | Lenhart | 250/519.1 |
| 5,015,864 A | 5/1991 | Maleki | 250/516.1 |
| 5,115,140 A | 5/1992 | Rodriguez | |
| 5,626,540 A | 5/1997 | Hall | 482/69 |
| 5,704,881 A | 1/1998 | Dudley | 482/69 |
| 5,981,964 A | 11/1999 | McAuley et al. | 250/515.1 |
| 6,281,515 B1 | 8/2001 | DeMeo et al. | |
| 6,448,571 B1 | 9/2002 | Goldstein | 250/515.1 |
| 6,459,091 B1 | 10/2002 | DeMeo et al. | |
| 6,653,648 B2 | 11/2003 | Goldstein | 250/515.1 |
| 6,828,578 B2 | 12/2004 | DeMeo et al. | |
| 6,841,791 B2* | 1/2005 | DeMeo et al. | 250/515.1 |
| 6,954,968 B1* | 10/2005 | Sitbon | 24/303 |
| 7,319,400 B2* | 1/2008 | Smith et al. | 340/573.1 |
| 2005/0211930 A1 | 9/2005 | DeMeo et al. | |
| 2007/0138415 A1 | 6/2007 | Rees | |

FOREIGN PATENT DOCUMENTS
DE    29 34 955 A1    3/1981

\* cited by examiner

*Primary Examiner* — Kiet T Nguyen
(74) *Attorney, Agent, or Firm* — Harper Law Group; Scott L. Harper

(57) ABSTRACT

A system for providing radiation protection is provided that includes a garment that contours to an operator's body. The garment protects the operator from radiation. The garment is supported by a suspension component that reduces a portion of weight of the garment for the operator, the garment including a belt, which includes a release mechanism that offers an entry into the garment. In more specific embodiments, the release mechanism is a quick release that allows the operator to disengage from the garment using a single hand movement. The belt can include at least one flexible joint. The belt opens to allow the operator to enter the garment, and the operator, in entering and exiting the garment, is able to limit his contact to components on or near a front of the garment such that the operator can operate the release mechanism for the garment without losing sterility.

10 Claims, 27 Drawing Sheets

ARTICULATING ARM ON TROLLEY

JIB CRANE

ARTICULATING BRIDGE CRANE

JIB CRANE

CABLES ATTACH TO TENSIONER AND QUICK RELEASE MECHANISM

TINY ROUNDED RIDGES AT EACH JOINT

QUICK RELEASE WITHOUT SWIVEL ASSEMBLED
54
52

50
ROD LEADS TO TOP OF HANGER
PIVOT POINT FOR PIN
WIDER FINGER PAD ON PIVOT PIN
SPRING PUSHING OUT
QUICK RELEASE BALL PIN
PIN GUIDE CUTOUT

LOWER PIECE FRONT CROSS SECTIONAL VIEW
52

LOWER PIECE SIDE VIEW
52
QUICK RELEASE PIN HOLE
GUIDE PIN

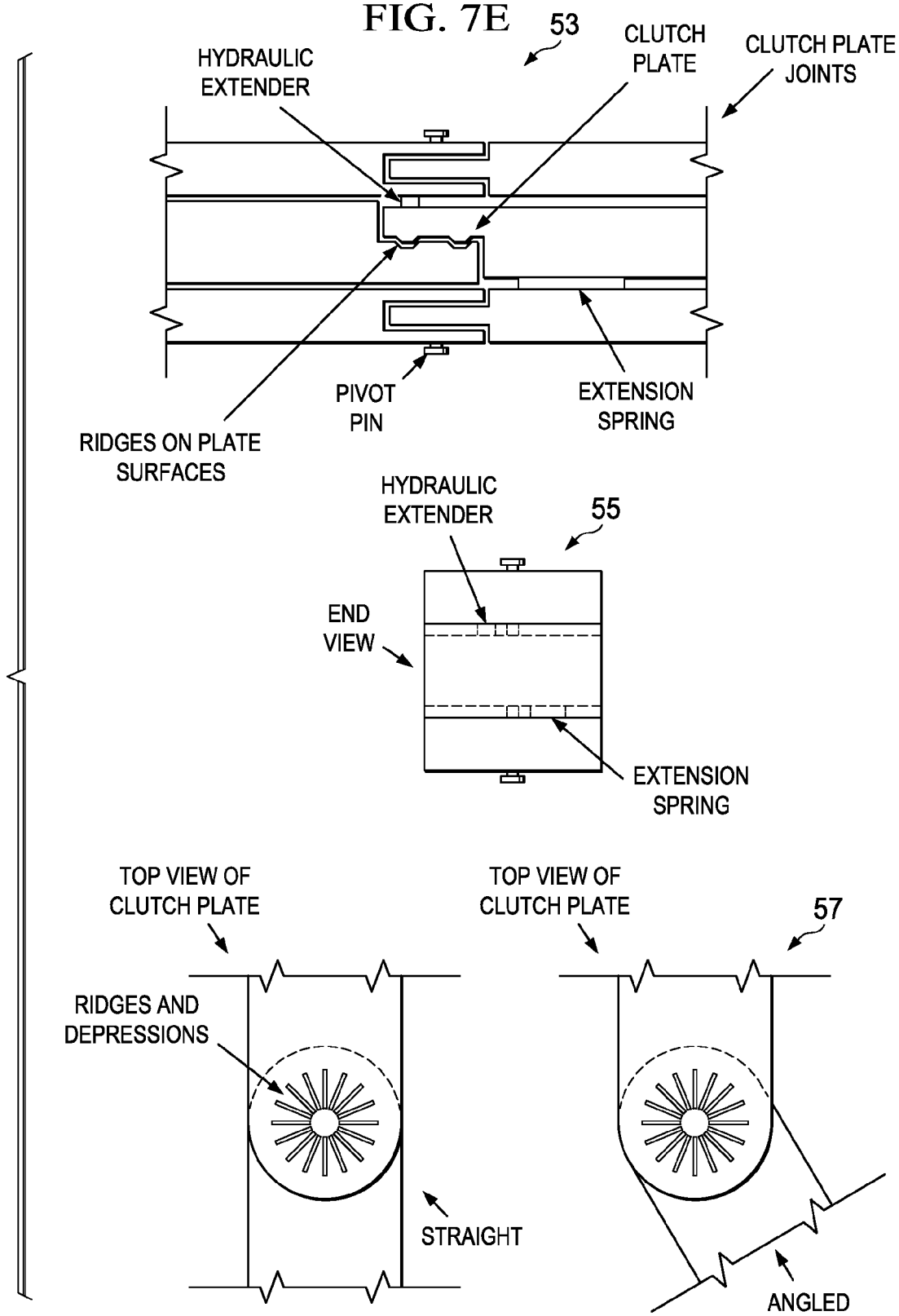

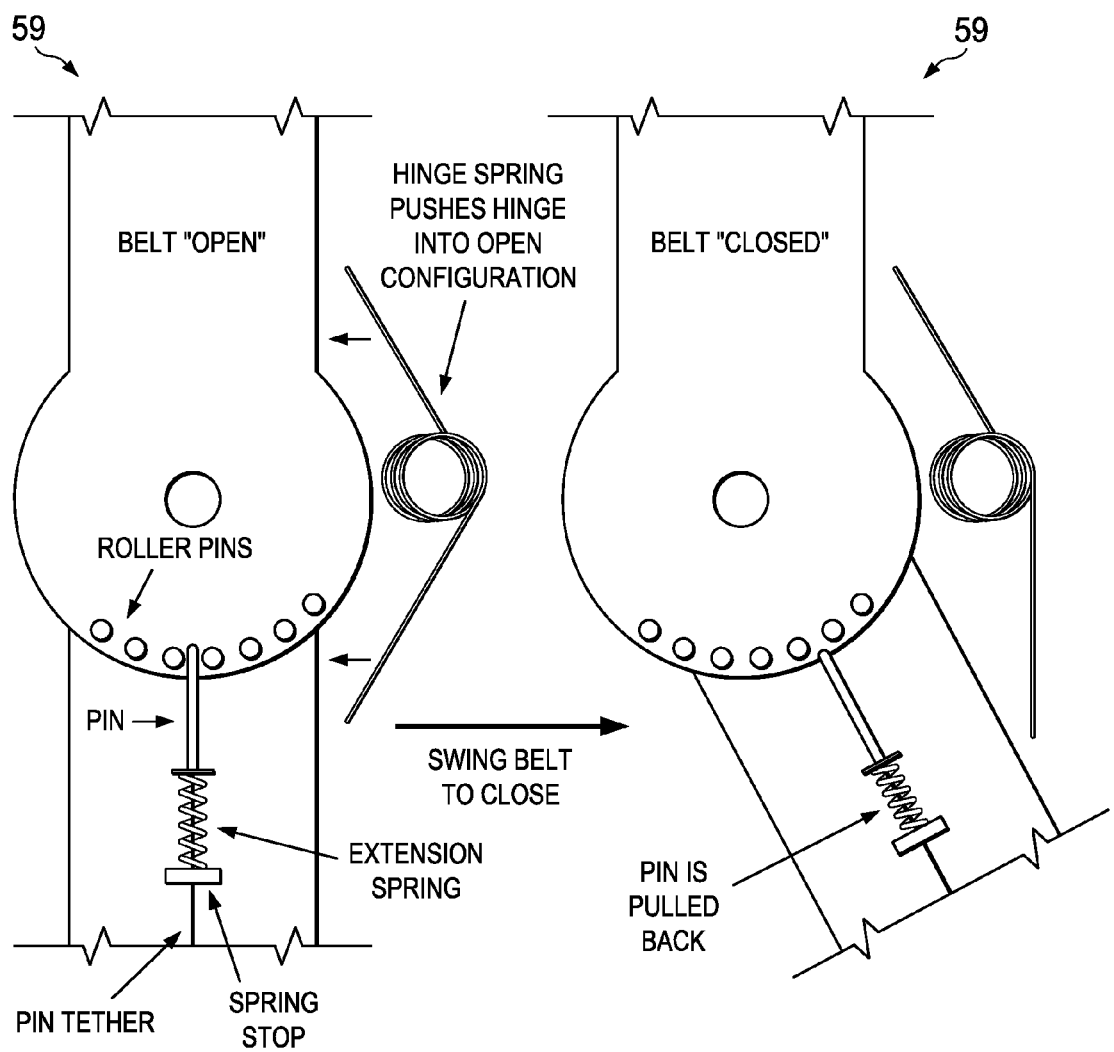

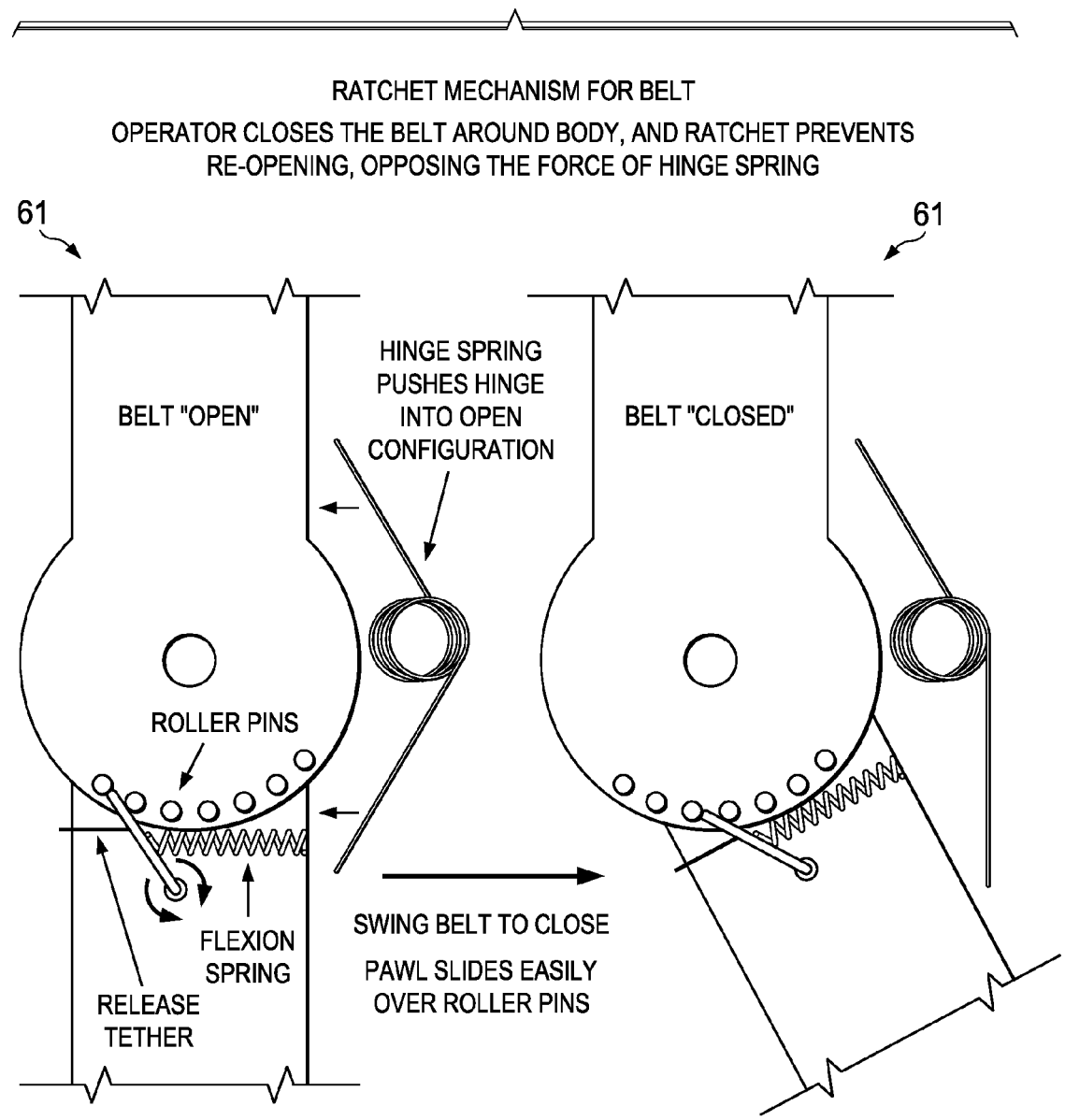

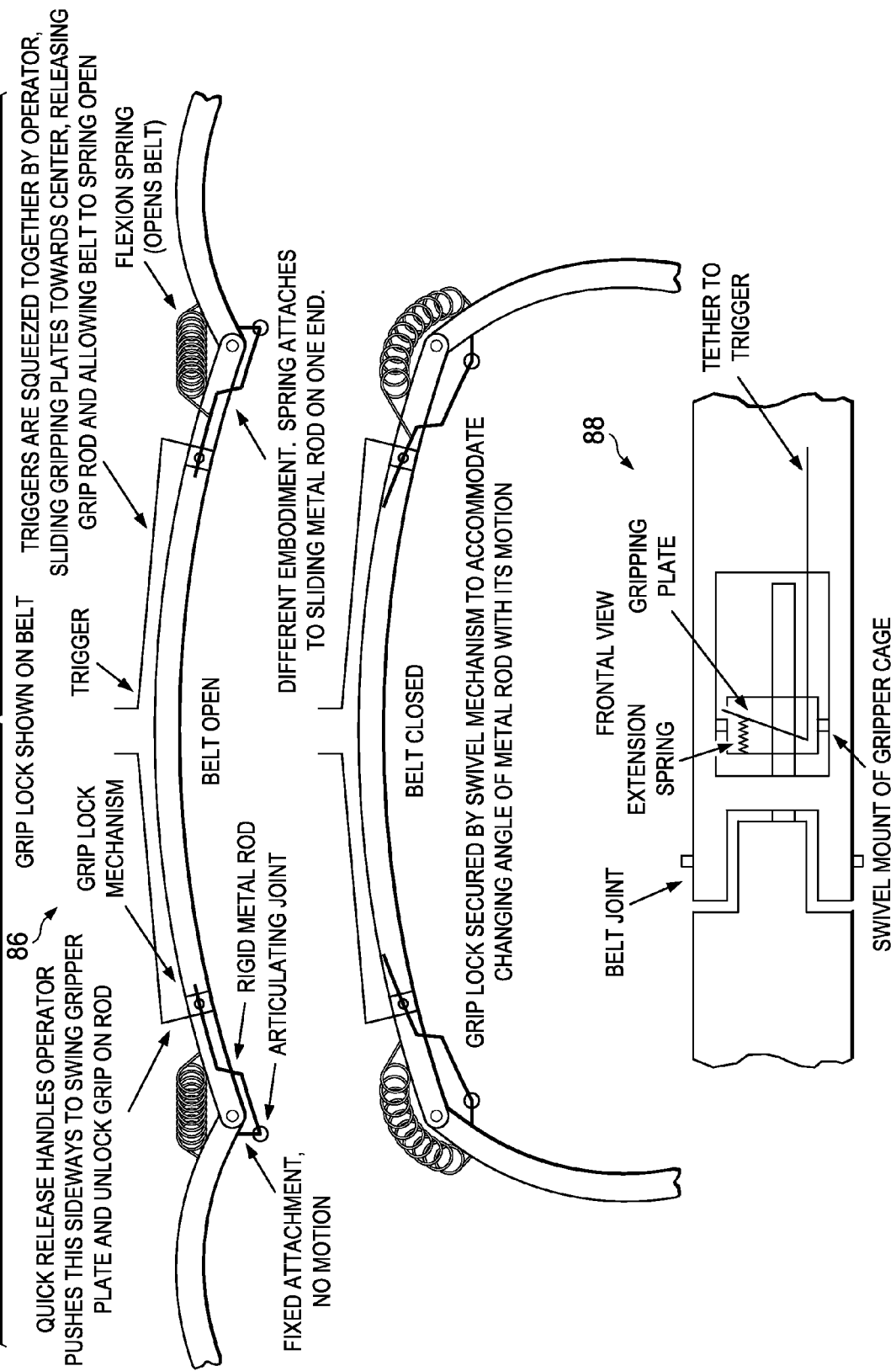

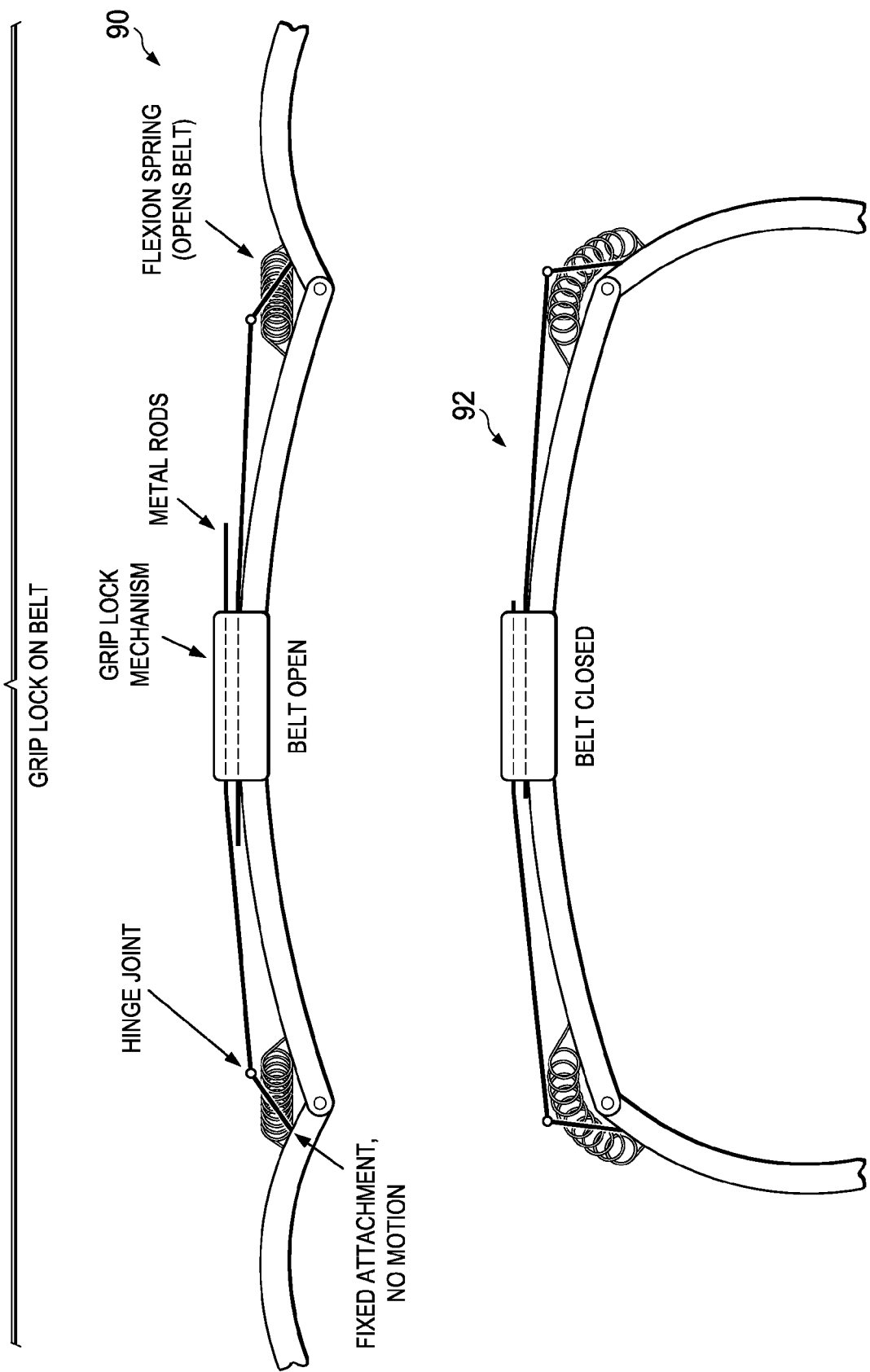

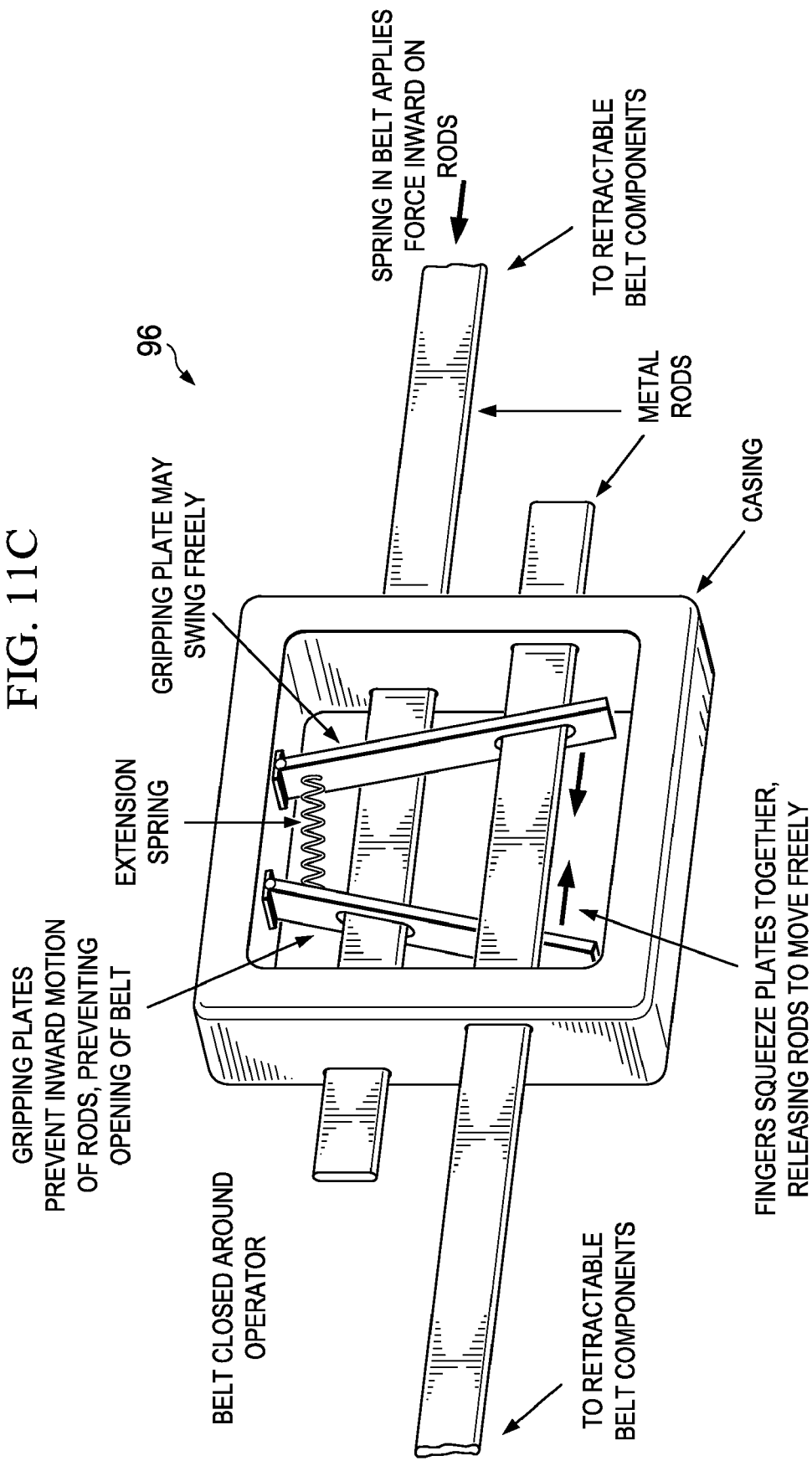

SYSTEM AND METHOD FOR PROVIDING A SUSPENDED PERSONAL RADIATION PROTECTION SYSTEM

This application claims priority under 35 U.S.C. §119 of provisional application Ser. No. 61/022,174 filed Jan. 18, 2008 entitled: Suspended Radiation Protection for Protection of Worker.

TECHNICAL FIELD OF THE INVENTION

This invention relates in general to radiation protection and, more particularly, to a suspended personal radiation protection system.

BACKGROUND OF THE INVENTION

Radiation is used to perform many medical diagnostic and therapeutic tests and procedures. Medical, veterinary, or research personnel may be involved in the performance of these procedures. These professionals are being exposed to scattered radiation as they perform their work. The long-term effects of this exposure are poorly understood at the present time, but are considered serious enough to warrant mandatory protection for operators, who are required to wear garments or barriers that contain materials, which absorb a significant proportion of the radiation. In order to properly treat patients, operators require freedom of motion. Providing a personal radiation protection garment that properly protects operators, while allowing operators to move freely and comfortably, presents a significant challenge for medical operators in radiation environments.

SUMMARY OF THE INVENTION

In accordance with the present invention, a method, a system, and an apparatus for implementing a suspended personal radiation protection solution are provided that substantially eliminate or reduce the disadvantages and problems associated with previous approaches.

In accordance with one embodiment of the present invention, a system for offering radiation protection includes a garment that contours to an operator's body. The garment protects the operator from radiation. The garment is supported by a suspension component that reduces a portion of weight of the garment for the operator, the garment including a belt, which includes a release mechanism that offers an entry into the garment.

In more specific embodiments, the release mechanism is a quick release that allows the operator to disengage from the garment using a single hand movement. The belt can include at least one flexible joint. The belt opens to allow the operator to enter the garment, and the operator, in entering and exiting the garment, is able to limit his contact to components on or near a front of the garment such that the operator can operate the release mechanism for the garment without losing sterility.

In still other embodiments, the release mechanism includes a spring mechanism that exerts a force on the belt. The garment allows the operator, who is wearing the garment, to move freely in X, Y, and Z spatial planes, and the garment can be substantially weightless to the operator. Further, the garment may include a sleeve on at least one side of the garment.

The garment can include a rapid, easy closure of the belt around the operator, potentially accomplished by manually squeezing the belt itself with the operator's arms and, thereby, closing it at its hinges and mobile joints. Alternatively, closure may occur when a cable arrangement or mechanical linkage is activated which draws the hinges closed. The easy opening of the belt enables an ideal exit for the operator: allowing the operator to only touch components on (or near) the front of the device in order to preserve sterility (i.e., the sterile condition of the environment). Typically, operator contact towards the rear of the device would result in a loss of sterility of the hands. The simple mechanisms of the garment require minimal gross hand and finger movements so that these operations can be accomplished through the sterile cover without unnecessary fumbling.

Such a device offers automation for the opening of the belt such that the operator need only activate a given quick release to exit the garment. The other motions may be automated and triggered by this initial activation. This feature could be accomplished by a spring mechanism (wire or gas springs) or similar tensioning mechanism that exerts a force on the belt, which results in opening.

The suspended personal radiation protection device includes a suspension component. The suspension component empowers the operator to move freely in the X, Y, and Z spatial planes simultaneously, while the protective radiation garment is substantially weightless to the operator. The suspension component is further operable to support a partial weight of the operator such that the operator can move around in substantially zero gravity, or (at a minimum) the operator bears just a portion of his total weight. The radiation protection device further includes an optional face shield, which is transparent to visible light: allowing unhindered vision while protecting an operator from radiation. Other unique components of the garment are detailed below.

Important technical advantages of certain embodiments of the present invention include optimally supporting the weight of a radiation protection garment worn by operators. Ironically, the suspension component allows radiation protection garments to be heavier and more comprehensive. As a result, radiation protection garments can protect larger areas of operator's body and be constructed thicker to increase X-ray attenuation. Increased radiation protection reduces an operator's risk of cancers, cataracts, skin damage, etc.

Other important technical advantages of certain embodiments of the present invention include reducing the risk and incidence of musculoskeletal injuries from wearing heavy radiation protection garments. Operators using the present invention have normal freedom of motion, as if the operator is not wearing heavy material. Furthermore, the suspension device supports a majority of the operator's weight such that operators can work for longer periods without fatigue.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

To provide a more complete understanding of the present invention and features and advantages thereof, reference is made to the following description, taken in conjunction with the accompanying figures, where like reference numerals represent like parts, in which:

FIGS. 7A-7I are simplified block diagrams that illustrate example release components of the personal radiation protective garment in accordance with embodiments of the present invention;

FIGS. 11A-11C are simplified block diagrams that illustrate example grip lock components of the personal radiation protective garment in accordance with embodiments of the present invention.

DETAILED DESCRIPTION OF THE INVENTION

Figure 1:
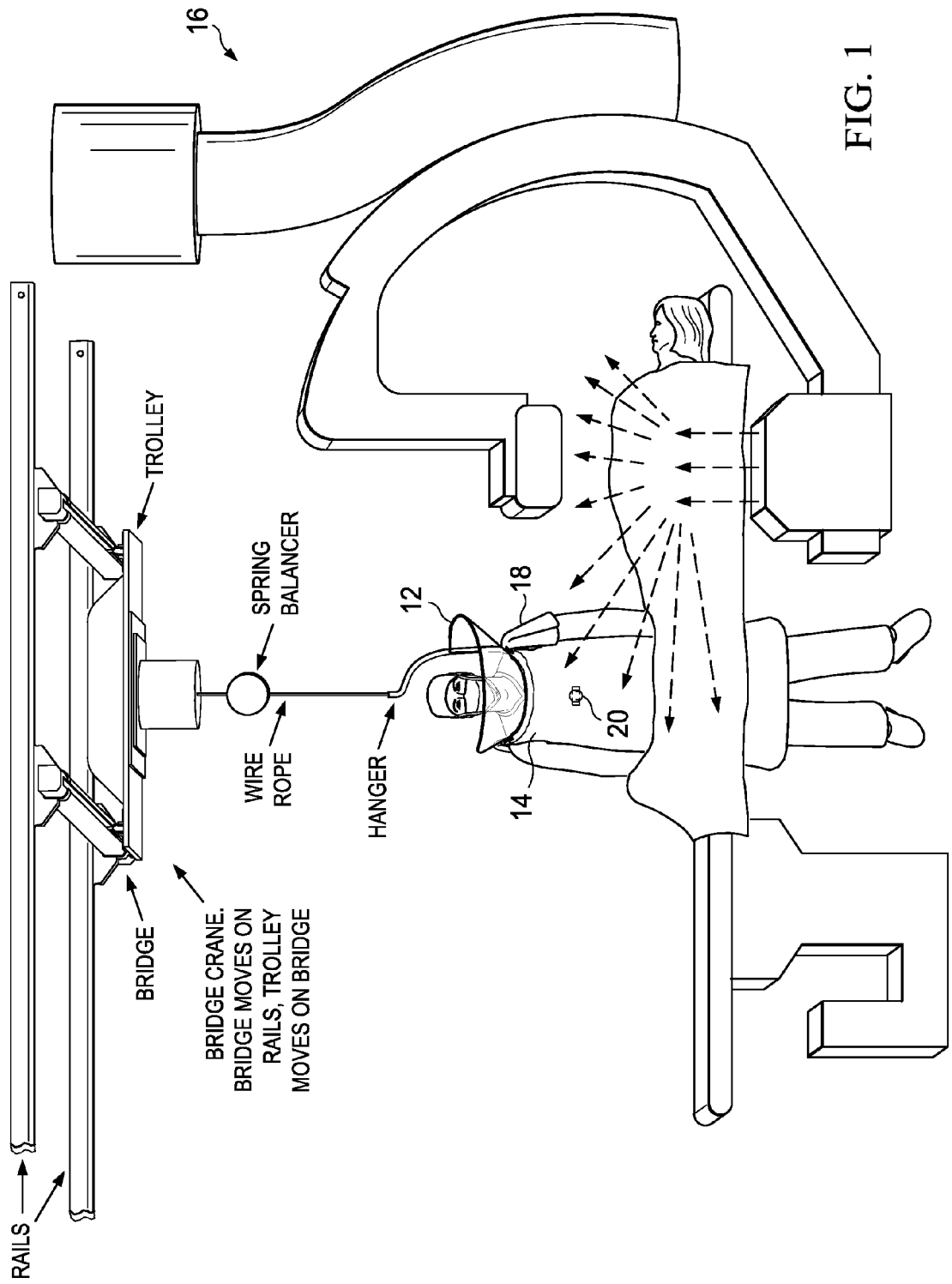
FIG. 1 is a simplified block diagram that illustrates a suspended personal radiation protection system in accordance with a particular embodiment of the present invention.

For purposes of teaching and discussion, it is useful to provide some overview as to the way in which the following invention operates. The following foundational information may be viewed as a basis from which the present invention may be properly explained. Such information is offered earnestly for purposes of explanation only and, accordingly, should not be construed in any way to limit the broad scope of the present invention and its potential applications.

Radiation is used to perform many medical diagnostic and therapeutic tests and procedures. The human patient or animal is subjected to radiation using minimal doses to enable completion of the medical task. Exposures to radiation are monitored to prevent or reduce risks of significant damage. Medical, veterinary, or research personnel may be involved in the performance of such procedures in great numbers.

Over many years, these professionals are being exposed to scattered radiation as they perform their work. Although their daily exposure is generally less than that for the patient, there are adverse cumulative effects to the operators. These long-term effects are poorly understood but are considered serious enough to warrant mandatory protection to workers in the form of garments or barriers that absorb a significant proportion of the radiation. There is a wide variety of such barriers commercially available, but these solutions have significant limitations for the operators who must come in close contact with the subject. These operators may be physicians and their assistants, or technically skilled medical personnel, who perform simple or complex medical procedures using their bodies and hands in proximity of the patient. In many cases, scatter radiation from the subject or physical elements in the direct radiation beam will pose significant health risks and unacceptably high exposure.

Risks of radiation exposure at the levels of medical personnel include cancers, cataracts, skin damage, etc. A review of current protective systems outlines their limitations. Radiation-absorbing walls are useful to contain the radiation to a room, but do not prevent exposures within their confines. Barriers within the room [such as floor or ceiling supported shields] are effective at blocking radiation for personnel who are not in close contact with the radiation field [such as some nurses and technologists] but must be positioned or repositioned frequently when personnel move around the room. They also provide cumbersome interference for operators performing the actual medical procedure. They may also be difficult to keep sterile when attempting to use them within the sterile field.

The most commonly used protection for operators involves the use of garments containing radiation-absorbing materials, generally lead or other metals, which are worn in the fashion of a coat, smock, skirt, vest, etc. and do not contaminate the sterile field because they are worn underneath the sterile covering gown. These garments are heavy and uncomfortable, and their long-term usage is known to be associated with diseases of the spine [in the neck and back], knee disorders, and other musculoskeletal problems, which can result in disability, medical expenses, and decreased quality of life for the operator.

The trade-off between protection and garment weight results in the frequent use of garments that do not cover the legs, head, torso, and eyes optimally, and may provide sub-optimal radiation protection due to the thickness of the metallic material being limited by the tolerability of the operator. To protect other radiation-sensitive tissues [such as the corneas of the eye and the thyroid], special heavy glasses containing metallic compounds and a collar around the neck are often worn. Even when the operator is encumbered with these items, the base of the skull [which may contain sensitive bone marrow] and the face are still unprotected. Personal face and neck shields address this problem, and are commercially available, but are rarely worn due to their cumbersome nature and heavy weight.

Such problems have been present for many years and there are current solutions that attempt to address them. Modifications to floor-supported mobile shields appear to attempt to provide improved dexterity for the operator relative to the standard bulky mobile barrier, and a floor support system with a modified garment design also attempts the same. However, they are still obstacles to free movement of the operator. Another system of barriers (such as those referred to as radioprotective cabins) around the patient has been proposed, but that appears cumbersome, confining, and inhibitory to operator movement both gross and fine, patient/subject contact, and sterile field operation.

Ceiling mounted barriers around the patient also appear to limit contact between patient and operator, and may make control of a sterile field difficult. One configuration includes a ceiling mounted device, which supports the weight of a lead garment, involving a dolly movable in one linear axis, with or without an extension arm that rotates around a central point on the dolly. Such mechanical configurations are in place for other types of suspended barriers and their motion mechanics may not be well suited for use with something attached to the operator's body since the operator must frequently move rapidly and freely in all three spatial axes. Typically, the operator will walk in unpredictable and rapid patterns over an operating area. One configuration includes the garment being suspended by a simple expansion spring, which will provide uneven forces depending on its degree of expansion occurring with operator motion [due to the nature of its simple spring mechanics]. It may also result in harmonic motions that affect operator dexterity. In addition, failure of the spring due to cycle stresses could lead to operator injury. In addition, location of the spring in a vertical direction above the operator could result in limitations due to ceiling height. Integration of the system with the heavy image intensifier monitor screen could further encumber the operator from normal motion.

A discussion of the types of motion performed by operators during their work is relevant. Operators generally stand next to an operating table where the patient is positioned. They often reach over the patient to various parts of the body, and they may lean forward while reaching for items, surfaces, etc. This puts stress on the spine when heavy garments are worn. They may bend or stoop, but rarely is this possible because the workspace containing the patient limits vertical motion. In addition, most procedures involve a sterile field where the operator's hands, arms, and torso [from neck to waist] must remain confined, so excessive vertical motion is prohibited. The operator may move considerably in the X and Y plane, which is horizontal and parallel to the floor, by walking or turning their body. The operator requires freedom of motion in these directions.

Overhead cranes have been available for many years and are commonly employed in the materials-handling industry. The following is a description of a bridge crane. A bridge crane includes at least one bridge, and a trolley moving on the bridge, end trucks arranged at the ends of the main bridge to support the main bridge, wheels arranged to the end carriages intended to move along substantially parallel rails substantially parallel to the end trucks. Smaller cranes [such as those to be used to support a load up to 250 pounds] are often operated by workers without the aid of motorized assistance because the crane's movable parts are light enough to be manipulated by hand. Different systems are employed to suspend the load from the cranes, including hoists, balancers, and intelligent assist devices.

Tool balancers are also currently available and help to suspend tools in the workspace in a manner that provides ergonomic benefits for workers using them. The tool balancer is generally attached over the workspace, and reels out cable from which the tool is suspended. Adjustments may be made to provide a "zero gravity" balancing of the tool at the desired height such that the worker may move the tool up or down within a working range without having to bear a significant portion of the tool's weight. Adjustments may cause the tool balancer to exert a stronger upward force such that the operator must apply a downward force on the tool to pull it down to the workspace and the balancer will cause the tool to rise when the operator releases it.

Tool balancers may be of the spring or pneumatic variety, referring to the mechanism, which provides the force for its operation. A spring tool balancer, such as in the preferred embodiment of this invention, generally contains a coiled flat spring [similar to a clock spring], which is attached to a reel with a conical shape and which serves as the platform for the winding of the cable. The conical shape provides a variable mechanical advantage, which offsets the variance of the force provided by the spring as it winds or unwinds. The result is a relatively constant force on the cable within a definable working range. Safety concerns mainly involve falling objects, strength of the suspension device, strength of the cable, and operator falls. The balancer can be attached to the trolley by its own hook and a safety chain. The suspension device is commercially available at specified maximum loads, which include a wide safety margin. The mounting of the suspension device will be done according to architectural standards.

Detachment of the garment from the suspension system will require certain care. A cable stop will prevent the hanger from going higher than the set level. Some balancers are equipped with a locking mechanism that prevents motion of the cable during load change or removal. This permits simple removal or exchange while standing at ground level. Alternatively, without activating a locking mechanism, The worker could stand on a step stool and lift the load upwards until it contacts the balancer stop, and then remove the garment without concern for sudden upwards, uncontrolled motion of the balancer cable and hanger. Alternatively, a weight, which is approximately equivalent to the weight of the garment, could be attached to the hanger prior to disengaging the garment. This will drop the garment and require it to be supported by the worker, who may then disengage it from the hanger. The weight will prevent any upward motion of the hanger in an uncontrolled manner. The next time the garment is attached, the weight could be removed after secure attachment of the garment is confirmed.

For most operations, the garment need not be detached from the cable. It could be left suspended and moved out of the way of other activities. Another alternative method would involve setting the force on the balancer to be slightly greater than the weight of the garment. Once removed from the body, the garment would then slowly and safely rise up until stopped by the cable stop. Upon next use, it could easily be pulled back down into position. Annual inspections of the system may be performed for cable frays, hook lock malfunctions, and rail component flaws.

In the event of an operator fall, it is unlikely that the system will contribute to operator harm since the balancer cable is long enough to allow the operator to reach the floor. Any harm to the operator should be the same as if not attached to the cable, except perhaps for some beneficial effect of the upward force of the suspension system.

In the event of spring breakage, most balancers are equipped with automatic cable locking mechanisms to prevent dropping of the load. In the event of cable or fastener breakage, the frame of the garment/hanger may be designed such that there are pads over the shoulders of the operator which would gently engage the operator's shoulders to support the weight of the device, which is approximately equivalent to a moderately heavy backpack. This latter malfunction should be avoidable with adequate cable and fastener strength and annual inspections.

In the event that rapid detachment of the operator from the system is necessary due to emergency, this can be achieved by a simple removal of the garment from the body without detachment from the system. The garment can be left hanging, and the suspended garment can be moved to the end of the runway, clear of the moving patient or stretcher.

Turning back now to the general problem of radiation, it is evident that people are often exposed to radiation in the course of their work. The proposed concept, outlined herein, describes a device and technique intended to address many of the aforementioned problems. It provides extensive shielding for the operator: covering a large part of the body. The shielding capacity can be increased with thicker, heavy metal layering, thus reducing a dose to the operator because the device is weightless [or nearly so] to the operator. The device is close to the body of the operator, much like a conventional apron, however it is not supported by the operator. It moves with the operator as he/she moves around within the working field and sterile field, and allows movement of arms and body parts to accomplish the procedure at hand.

The overall effects of the device are: improved comfort for the operator who is no longer supporting heavy-shielding clothing, improved radiation protection to an operator through a much greater portion of body shielding [compared to a conventional apron], as well as more effective shielding of much of the covered parts due to greater use of the shielding material. This approach also offers a musculoskeletal benefit due to the absence of a significant weight burden on the operator.

FIG. 1 is a simplified block diagram of a suspended personal radiation protection system 10. System 10 includes an operator, a patient, a radiation source 16, radiation rays, a component (detailed in subsequent FIGURES), and a release 20 for the personal radiation protection garment. The garment includes a face shield 12, an outer apron 14, and a sleeve element 18. Each of these components is outlined in greater detail below with respective FIGURES that further highlight some of their potential intricacies and capabilities.

Figure 2:
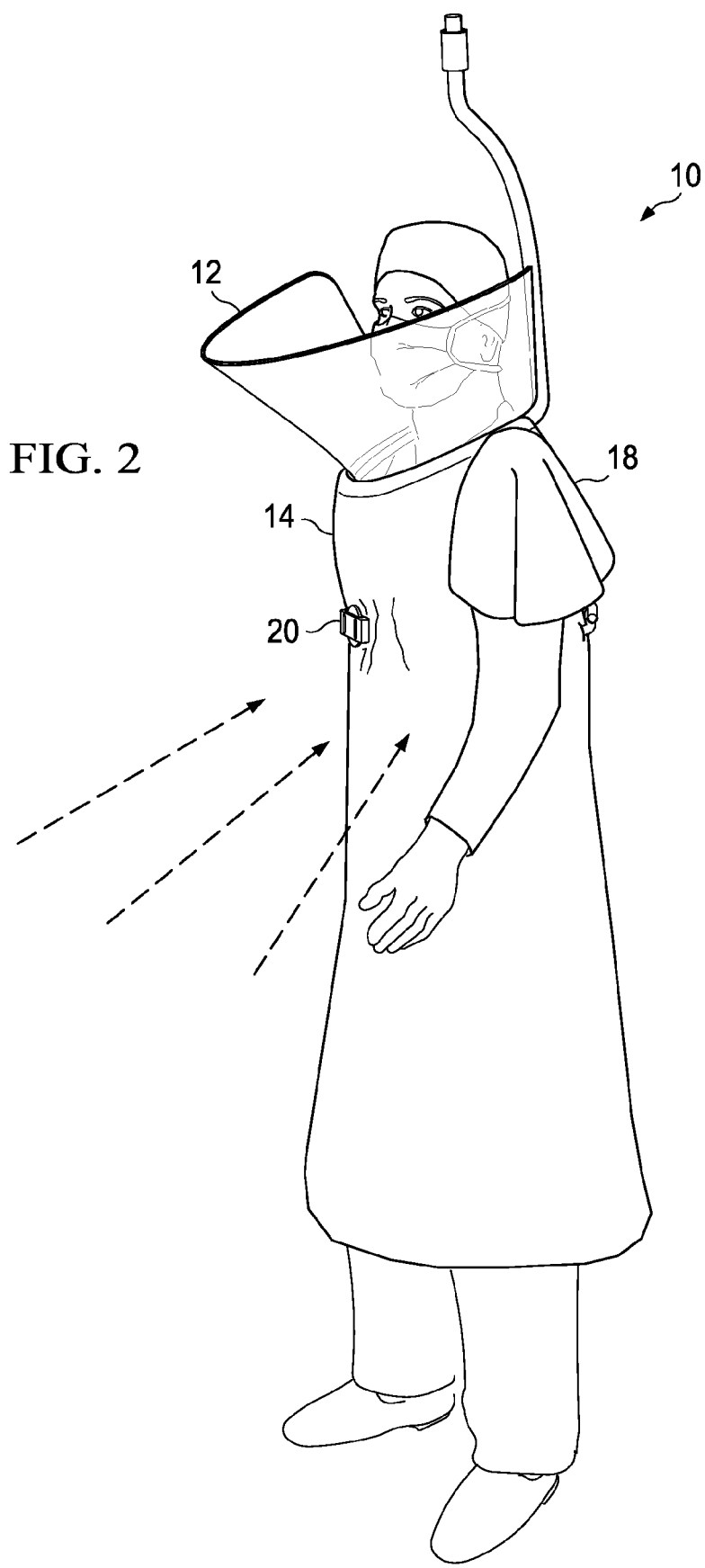
FIG. 2 is a simplified block diagram that illustrates a side view of a personal radiation protective garment in accordance with a particular embodiment of the present invention.
Figure 3:
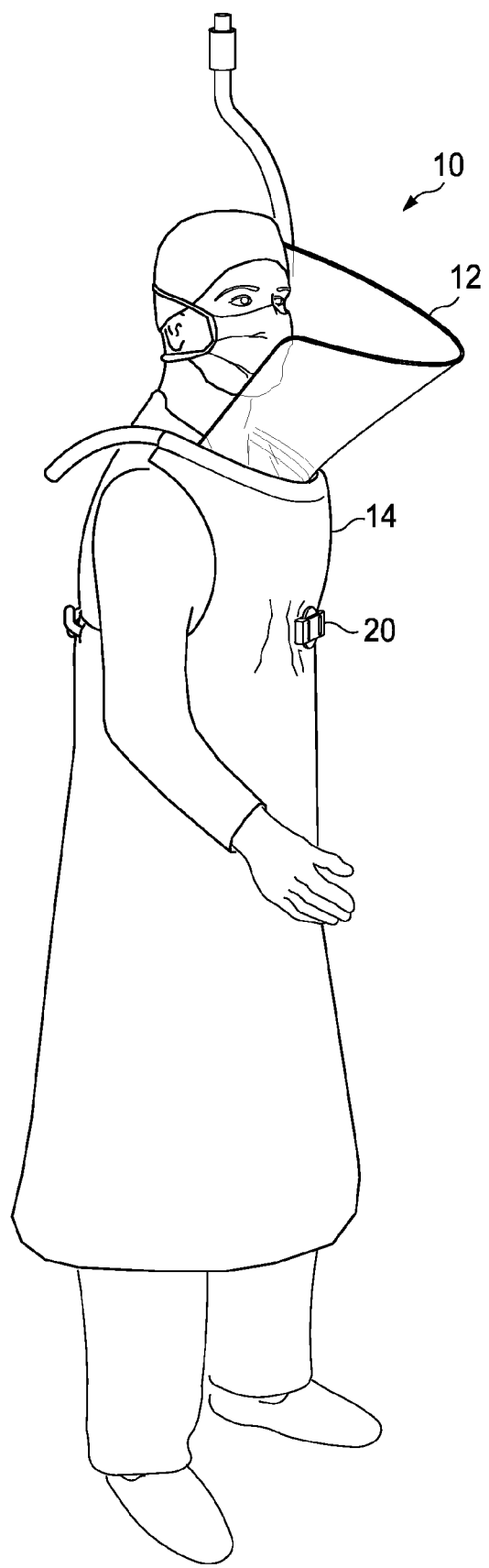
FIG. 3 is a simplified block diagram that illustrates another side view of the personal radiation protective garment in accordance with a particular embodiment of the present invention.

In general, the garment and shield 12 are suspended from a hanger, which is supported by a given suspension component. [Other example suspension components are outlined below with reference to FIGS. 5A-5L.] FIGS. 2-4 further illustrate this garment architecture from side and front views. An operator can position himself in the garment such that the operator is not supporting the weight of the garment. In this sense, he is liberated from the typical and problematic weight constraint. While using radiation to treat a given patient, the operator can move freely in the X, Y, and Z spatial planes such that the garment and shield 12 are substantially weightless. (Note that U.S. patent application Ser. No. 11/611,627 entitled "System and Method for Implementing a Suspended Personal Radiation Protection System" is hereby incorporated by reference herein.)

In accordance with the teachings of the present invention, suspended personal radiation protection system 10 achieves an effective way for operators to protect themselves properly and comfortably from harmful radiation. System 10 consists of a framework of rigid components (such as steel for example) with some components allowing motion in various types of joints. Such design choices permit the support of a pliable component such as fabric containing heavy metals to absorb radiation. The absorption materials are positioned close to the operator and are in the pathway of scattered radiation. Also provided to the garment is an optimal face shield 12 that offers an optically transparent (or nearly transparent) component (such as leaded glass or acrylic). The shield is proximate to the operator's face, neck, and head, but distant enough to reduce potential fogging.

Figure 5A:
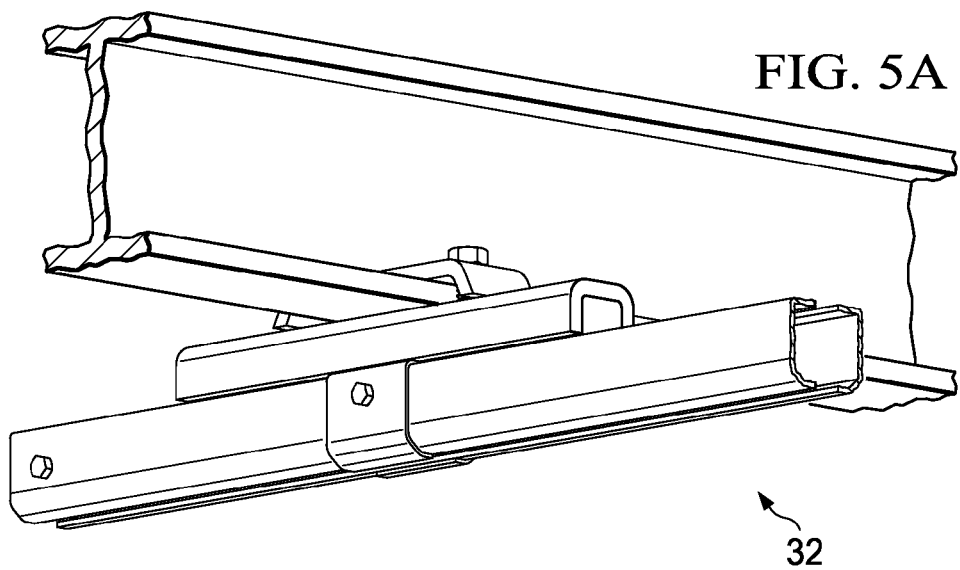
FIGS. 5A-5L are simplified block diagrams that illustrate example support options that can be integrated with the personal radiation protective garment in accordance with particular embodiments of the present invention.
Figure 5B:
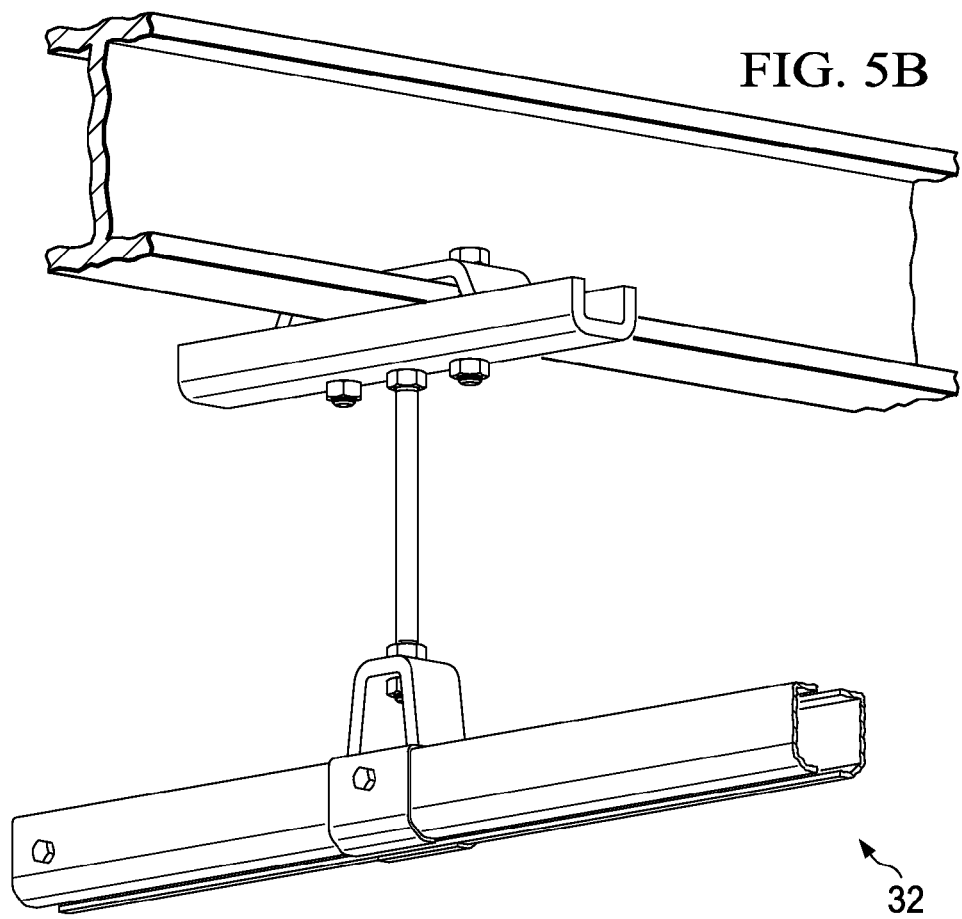
Figure 5C:
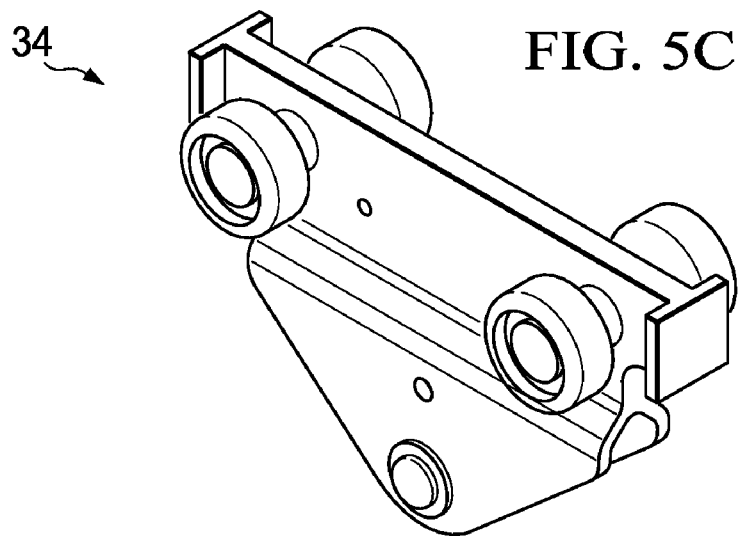
Figure 5D:
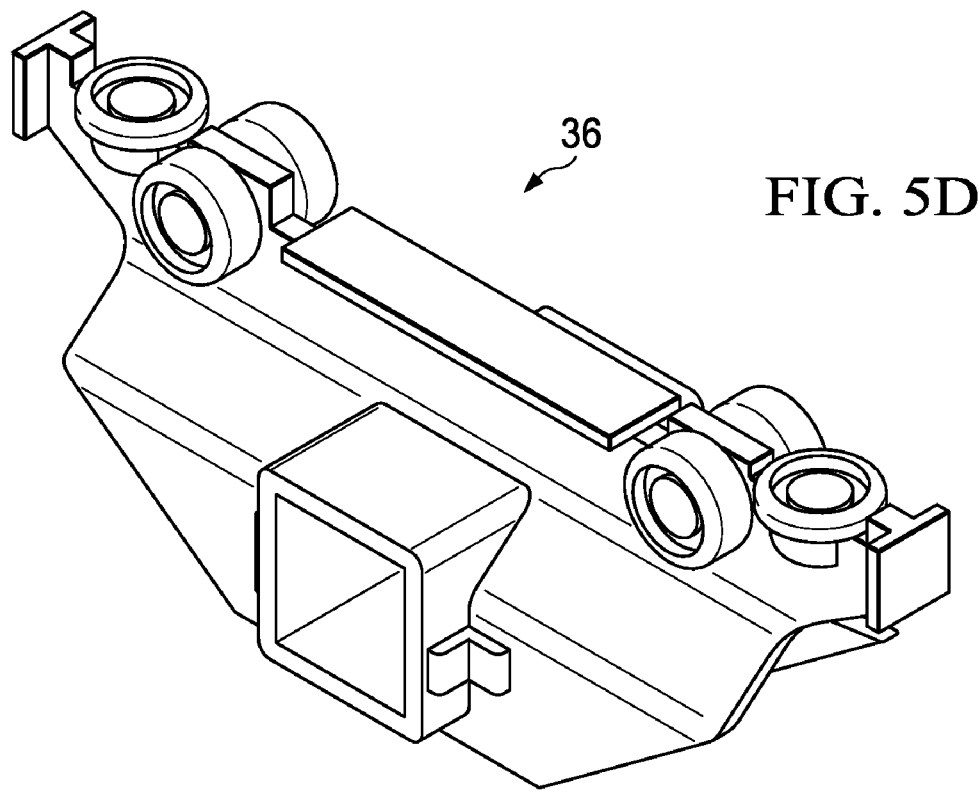
Figure 5E:
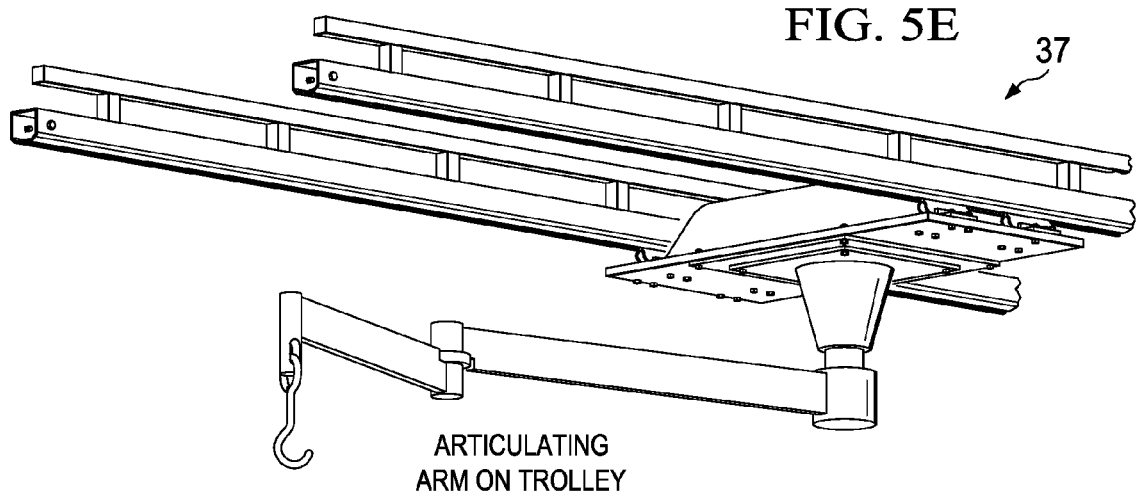
Figure 5F:
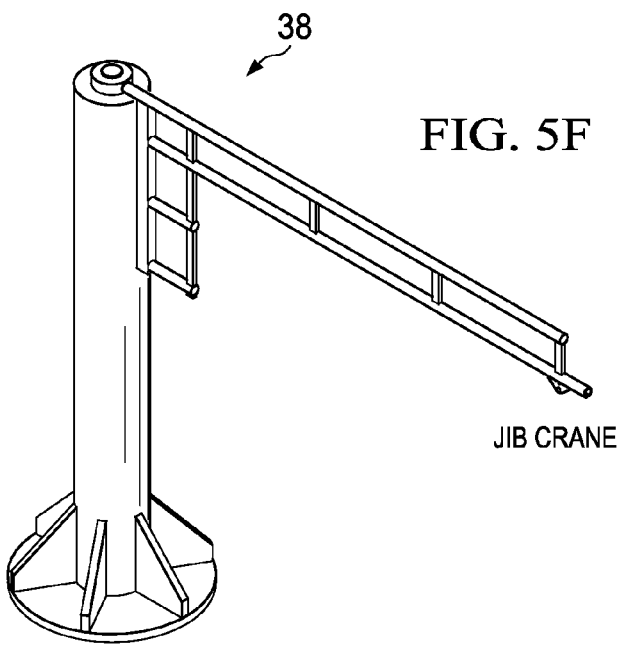

FIGS. 5A-5L illustrate how the garment can be supported by an overhead structure such as the ceiling, a floor-supported frame, a telescopic arm, or a table supported frame. Specifically, FIGS. 5A-5B illustrate an overhead support structure 32, while FIGS. 5C-5D depict trolleys 34 and 36 that can slide on a given set of rails. FIG. 5E illustrates a support 37 that offers a trolley that may slide along rails affixed to the ceiling. The trolley contains an articulating arm that may extend beyond the confines of the ceiling mounted structures. FIG. 5F illustrates a jib crane 38 where the trolley slides on an arm, which rotates on the floor mounted pivot stand. This allows positioning under a wide arc.

Figure 5G:
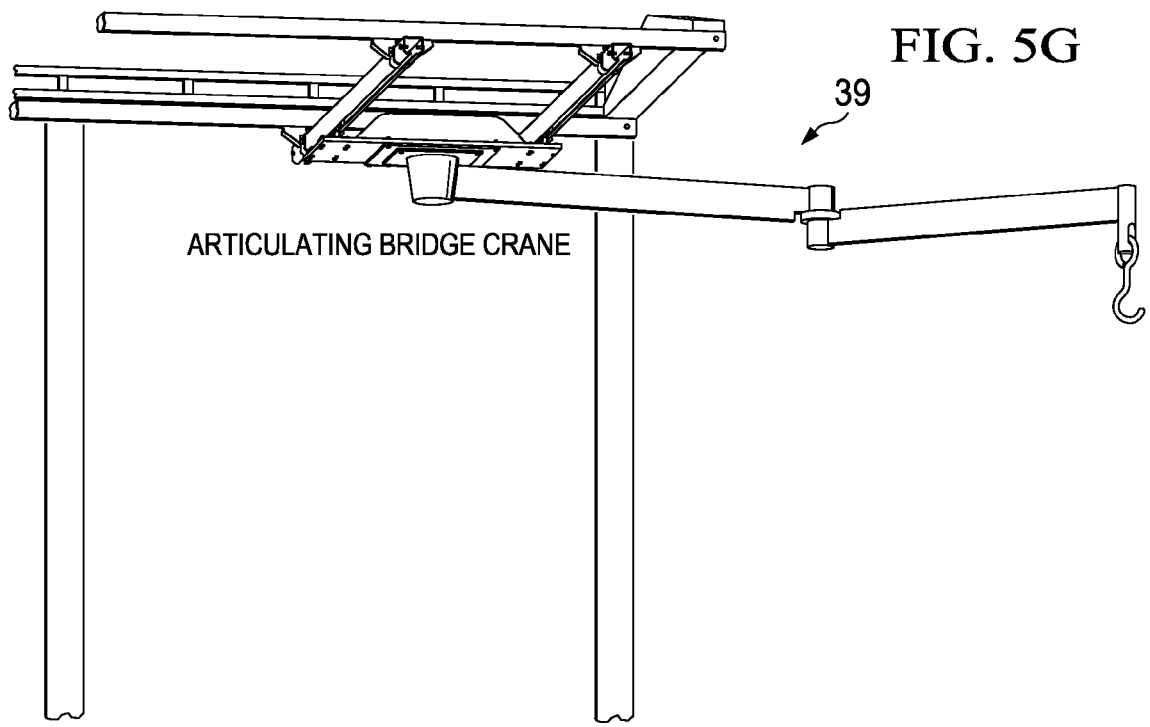
Figure 5H:
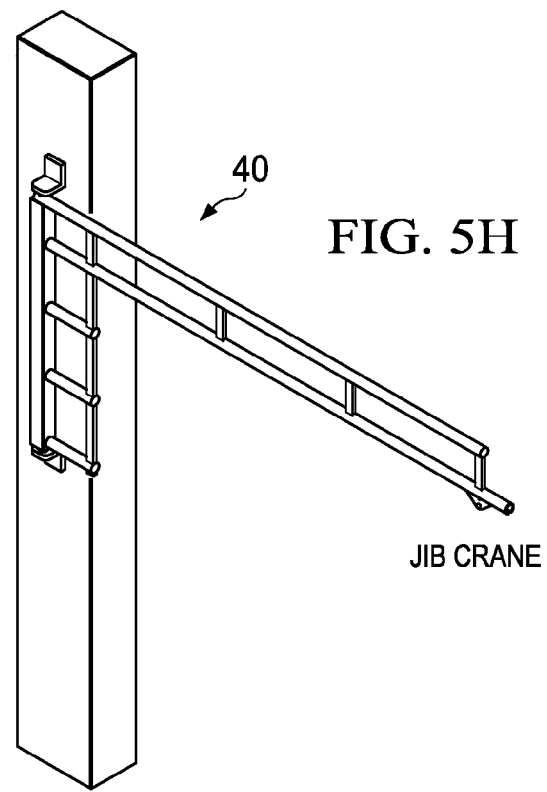
Figure 5I:
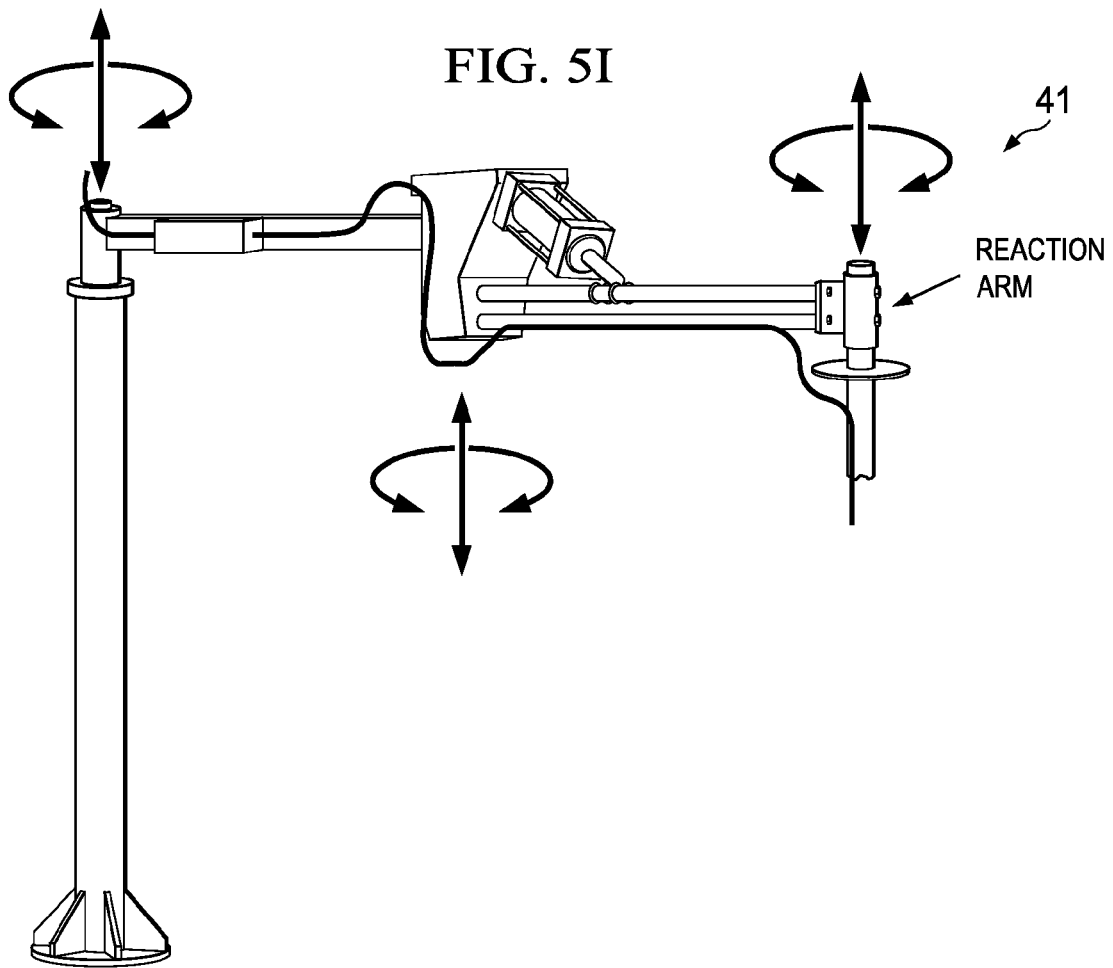
Figure 5J:
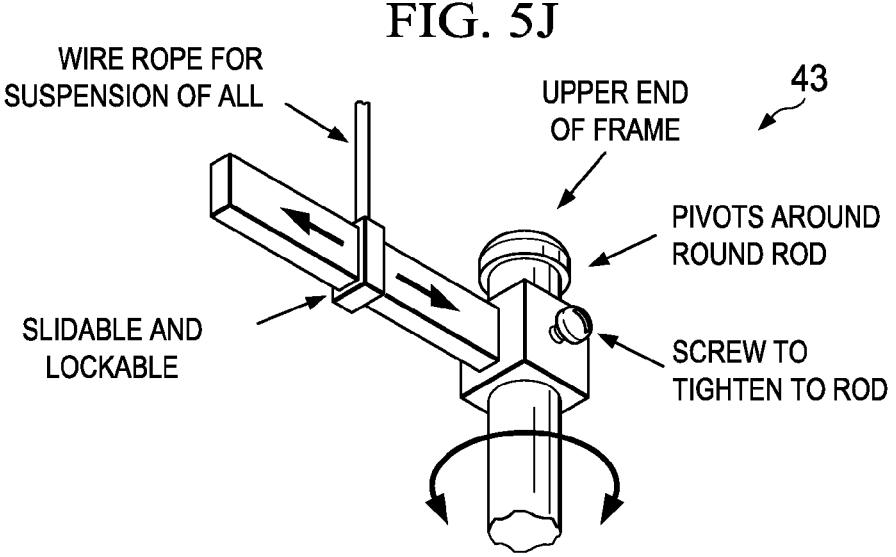

FIG. 5G illustrates a support 39 that offers an articulating bridge crane. The bridge moves along stationary rails in the ceiling and the trolley moves along the bridge. In addition, the articulating arm permits extension outside of the ceiling mounted rails. FIG. 5H illustrates a support 40 that offers a jib crane. The trolley slides on a swinging arm in this embodiment, which is wall mounted. Such an arrangement can readily be ceiling mounted and it too allows positioning under a wide arc. FIG. 5I illustrates a support 41 that is a reaction arm. This could be power-assisted and absorb shock and torsion forces, if necessary. FIG. 5J illustrates a support 43 that offers a hanger and swivel pivot for adjustment of the center of gravity. In this embodiment, there is a screw provided to tighten the rod. Note that the wire rope is slidable and lockable. This telescopic configuration allows placement of the suspension point of the wire cable in any position under a large arc. This further allows balance of the whole device in any way desired.

For purposes of clarification, a few terms are outlined here to assist the readers in understanding some of the following descriptions. Suspension means or 'suspension component' can include a crane, ceiling mounted mechanisms, wire ropes, spring balancers, wire ropes, etc. This all leads to a wire rope that connects to a hanger. The hanger hangs from the suspension component by the wire rope of the spring balancer, in those embodiments employing a spring balancer, and is integrated into the device frame that sits on the shoulders and chest and that holds up the shield and apron, contains the belt, etc. In some of the tendered FIGURES, the hanger arcs from a position over the top of the head, down to the rest of the frame.

The device frame is the skeleton that contours around the shoulders and chest and torso and contains the belt mechanism. The frame supports the apron and shield and is integrated rigidly or with an articulation with the hanger. In an alternative embodiment, the hanger is not a rigid rod, but instead two wire ropes that connect to the frame and support it. These two wire ropes are suspended from a horizontal bar, which may have an adjustor on it that is attached to the suspension component (wire rope).

The term 'balancer' refers to [typically] a spring balancer. This is the zero-gravity support device that is integral to the suspension component and is what gives freedom of motion in the Z axis [while supporting the weight of the hanger/frame/rest of the device].

The hanger adjustor is one of many types of devices that permit balancing of the device in a different way than the "balancer." The device hangs from the wire rope like a mobile, so moving the point of attachment around in a plane horizontal to the floor within a small area over the operator's head will change how the device is oriented in space [i.e., how it tilts right to left or front to back].

The "hanger" is the portion of the frame of the device that arcs up over the operator's head, and holds up the apron and shield. In one example outlined in FIG. 5J, the object is on the top of the hanger, right over the head. The cable that comes down from the balancer attaches to it.

FIGS. 5A-I represent suspension components (for example "cranes" for the device) and related apparatus. These architectures shown (i.e., FIGS. 5E-5I) are alternatives to simple "bridge crane" scenarios, representing either non-bridge crane configurations with or without articulating arms, or in one case (FIG. 5G), a bridge crane with addition of an articulating arm. Another embodiment uses a bridge crane with a telescoping bridge that may reach further outside of the confines of the rails to allow more freedom of motion. Another example includes a framework similar to these cranes that is mounted on a floor-mounted framework instead of the ceiling or walls.

A spring balancer may hang from the tolley on the bridge. Attached to the end of the wire rope of the spring balancer may be the "hanger" portion of the device. The hanger may be a rigid structure that arcs over the operator's head, down to the frame that is approximated near his shoulders and torso and supports the face shield and body apron. At the top of this hanger, the attachment to the wire rope from the spring balancer may occasionally require adjustment in the X-Y plane in order to keep the device properly oriented in space, without tilting left to right or front to back. This adjustment may be made using several possible devices.

Figure 5K:
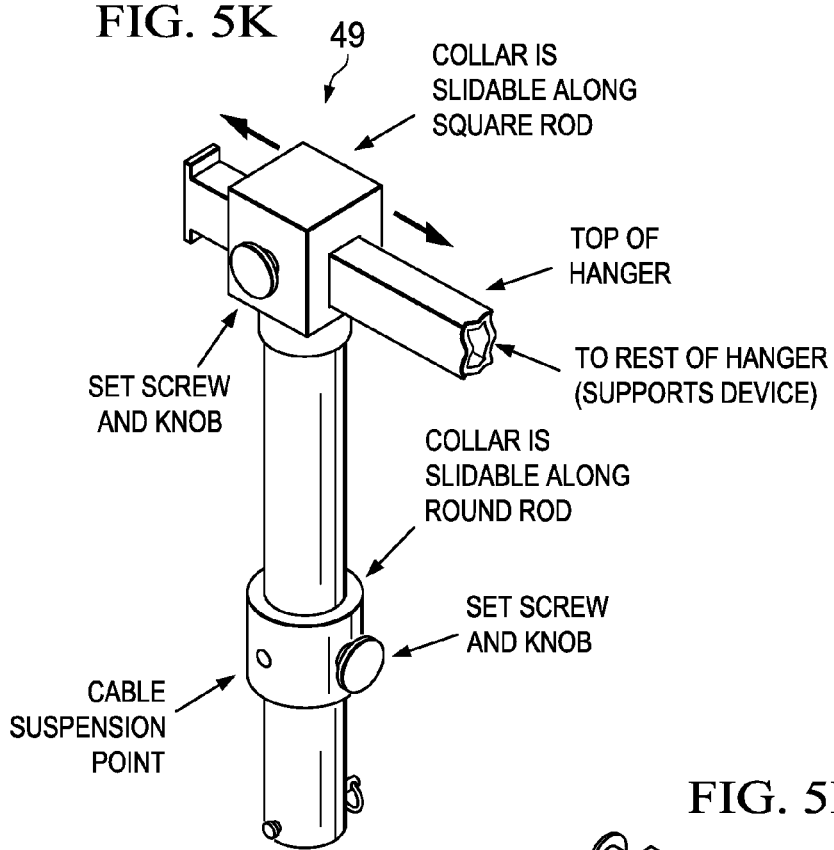
Figure 5L:
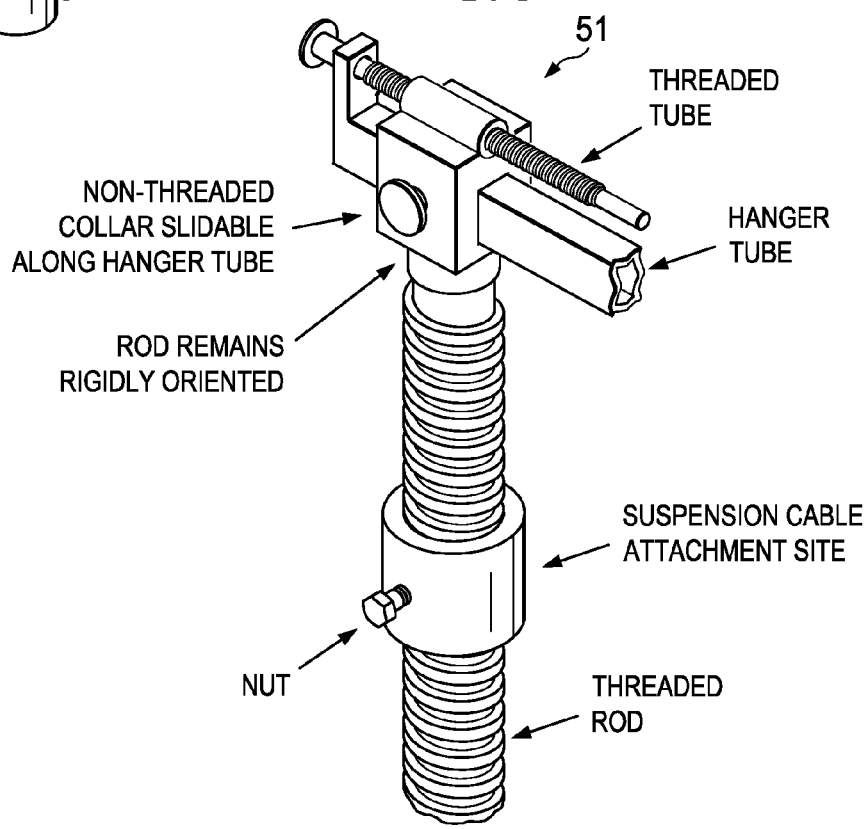

Turning now to FIGS. 5J-5L specifically, the device in FIG. 5J shows an attachment that allows pivoting of the horizontal bar of the hanger with slidable motion of the collar that attaches to the wire rope of the suspension system. This allows positioning of the suspension point within an arc above the hanging device, allowing positioning of the device in its neutral hanging position.

FIG. 5K shows a system 49 with components slidable in orthogonal directions (X and Y axes) allowing positioning of the point of attachment of the wire rope of the spring balancer or other suspension system in any position within a defined rectangular plane, resulting in the ability to tilt the suspended hanger and frame/apron/shield as needed for fit and comfort. In actual use, the square and round rods could be oriented in a plane parallel to the floor.

[Note that, as explained herein, the orientation of FIGS. 5K and 5L are illustrated slightly different than some of the included descriptions, in that the round rods are oriented vertically. Typically, these rods would be oriented horizontally, although the components are adequate. A person could just rotate them 90-degrees to put them in the same orientation as all the other FIGURES. This is just another example implementation of the possible alternatives encompassed within the present invention.]

FIG. 5L shows a similar system 51 with the addition of ball screw or similar threaded rod and nut arrangement that permits easy and precise movement of the components for easy positioning of the device in its neutral hanging position. In this configuration, the round rod may be rotated, causing the nut with the suspension cable attachment to move linearly as desired. Many other adjustor mechanisms are possible including a flat rectangular casing containing two ball screws oriented orthogonally to each other. One of them moves the other one slidable along the casing such that it can be positioned in many paths, all parallel to each other [i.e., both ends of it are moved equally up and down]. On this second ball screw is a threaded nut that moves along the screw as it is rotated. The suspension cable is attached to this nut. By rotating the two ball screws, the cable suspension point (on the nut) is, therefore, moved to any point in the X-Y plane inside the casing. In another mechanism, the second ball screw is substituted with a non-threaded rod which has a slidable collar with the cable attachment point. This collar can be slide manually, and a set screw locks it in place.

In another embodiment, there is a box-like casing with a cut-out in the plate that covers the top. This cut-out can be a grid pattern of many parallel rectangles that are connected in the middle by an orthogonally oriented cutout. A disc is slidable under the cutout, and is too large to be pulled through the cutout. Attached to the disc is the suspension cable, which passes through the cut-out. There is a locking mechanism, such as a cam-lock, which will lock the disc in place to prevent sliding. Adjustment is made by unlocking the lock, and sliding the disc to a location desired, then re-locking it. Alternatively, the cut-out pattern could be a spiral shape, and the disc could be slid anywhere along it.

Instead of a rigid arced rod, the hanger may consist of two cables that are suspended from a square or hexagonal or other non-round horizontal bar that hangs from the spring balancer wire rope. These two cables attach to the frame approximating the torso and shoulders and holding the shield and apron. Positioning of this device could be accomplished by attachment of the suspension wire rope to a horizontal rod (top cross bar) via a collar that can slide along the rod. This rod is oriented orthogonally to the square or other non-round shaped rod that is also horizontal, and gives rise to the two cables that suspend the frame of the device approximating the shoulders and torso and attached to the shield and apron.

The two cables attach to the frame in an adjustable manner, allowing front to back sliding and locking of the attachment points to the frame. Thus, between this adjustment, and the adjustment available in the hanger as described above, adjustment in the X-Y plane is possible. In this embodiment, stiff sleeves or tubes may be placed around the two lower cables in order to provide columnar support of the top cross bar, to prevent it from falling on the operators head in the event of suspension failure. Instead, it would fall forward or backward, away from the head, with diminished risk of injury. The bar could be expected to weigh less than one pound, and could be covered in a soft foam wrapping.

All of these implementation examples of the FIG. 5—set offer different mechanisms for attaching the device. In some cases, the device is hanging on the rigid hanger system in a manner that permits balancing of it: much like one would balance an artistic "mobile." By moving the attachment point of the cable to the rigid hanger, one can change/alter the balance somewhat. This balance adjustment may be helpful because changes to the lead apron or shield may throw the device slightly off-balance and cause it to tilt if the attachment point of the cable is not able to move from its "factory setting" of optimal balance. There are countless balance adjustments that could be used in conjunction with the present invention, which contemplates any such possible modifications or additions in offering an optimally balanced configuration.

An alternate form of suspension employs two cables that run on either side of the operator's head and that attach at approximately shoulder level to the rigid framework. Again, this is yet another example of a possible configuration that may alleviate particular concerns or that may overcome certain obstacles presented by specific circumstances/environments.

Generally, the aforementioned suspension components are used to allow motion in various directions while the garment's weight is supported in a "zero gravity" manner. These mechanisms can include a spring balancer (tool balancer), hydraulic balancer, counter balance system with weights, or constant force spring. Movement in the X and Y directions (in a plane parallel to the floor) is easily facilitated. The supported device that shields the operator may be configured to allow rapid exit and re-entry of the operator so that the operator may attend to other duties outside of the workspace area of the support system.

Another embodiment outlined above includes a rigid frame attached to the support cable. The part attached to the cable may be capable of complex motion relative to the lower part of the frame [at the level of the operator's head] to allow balancing of the device by placing the cable support location in many possible locations over the head. This may be accomplished in one form by an arm that can rotate around the vertical frame while remaining at a 90-degree angle, or other fixed angle, relative to the other portion of the frame to which it can move. This can be locked or secured in a fixed position when the desired location is found. The attachment site of the cable can slide along this arm. This allows for fixation at any point [within a large plane over the operator] to account for the desired balance and angulations of orientation of the device.

In regards to the actual device, the garment may contain radiation-absorbing materials, such as lead or other metals. The garment can be thicker and heavier than traditional radiation protection garments because the operator does not support the weight of the garment. Additionally, the garment can cover more of operator's body such as the operator's arms and legs, or less depending on particular needs. The garment can substantially contour to the operator's body or be loose based on specific parameters.

Thus, materials and/or components may be included in the garment in order to achieve the teachings of the protective, free moving, and weightlessness features of the present invention. However, due to its flexibility, the garment may alternatively be equipped with (or include) any suitable component or material, or any other suitable element or object that is operable to facilitate the operations thereof. Considerable flexibility is provided by the structure of the garment in the context of providing an adequate suspended personal radiation protection system.

Face shield 12 may contain radiation-absorbing materials such that it attenuates X-rays, but is transparent to visible light. Face shield 12 can be made heavier and it can curve or bend around the operator's face to cover more of the operator's face, as compared to traditional radiation protection face shields. Face shield 12 protects the operator from radiation approaching from the sides of operator's face and its design can be biased to one side of the face.

A fastening element of the garment can be positioned in the front, side, or rear of the garment. A belt design is described herein, but alternatively the garment can be opened and closed by Velcro, buckles, or any suitable fastening means for attaching pieces of a heavy material together. An assistant can fasten the Velcro or buckles such that the operator can quickly and effortlessly receive radiation protection from the garment that is substantially contoured to operator's body. The operator can wear a sterile gown and sterile gloves in the normal manner.

The belt configuration on the garment (as described in greater detail below) can include Velcro, buckles, or other fastening means such that the configuration helps secure the garment to the operator's body. The belt can be fastened on the front, side, or rear of the garment. The belt also helps the garment substantially contour to an operator's body such that operator's body is properly protected.

Velcro buckles or fastening means for adjusting the garment allow an operator to adjust the length of the garment. For example, a shorter person can fold up the excess garment material and fasten the garment such that the bottom part of the garment is double-layered. Similarly, a tall person can unfasten the double-layered area of the garment to receive more radiation protection on his legs such that the garment hangs to the operator's feet.

Sleeve 18 can be provided on the left or right arm [or neither arm] and sleeve 18 may contain radiation-absorbing materials such as lead or other metals. Sleeve 18 allows more protection coverage of the operator's body because the operator does not support the weight of the suspended sleeve. Sleeve 18 can also provide additional coverage for the side of the body that is most exposed to the radiation. Sleeve 18 may include a shoulder plate or harness underlying/reinforcing the sleeve configuration.

Figure 6B:
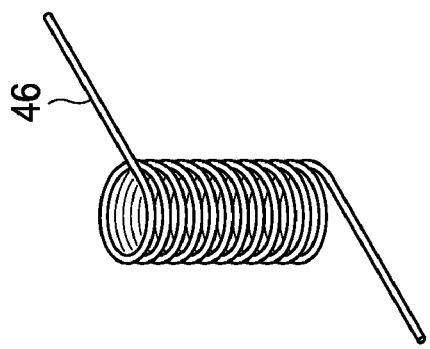
FIGS. 6A-6D are simplified block diagrams that illustrate example belt components of the personal radiation protective garment in accordance with embodiments of the present invention; Same as above FIG. 5
Figure 6A:
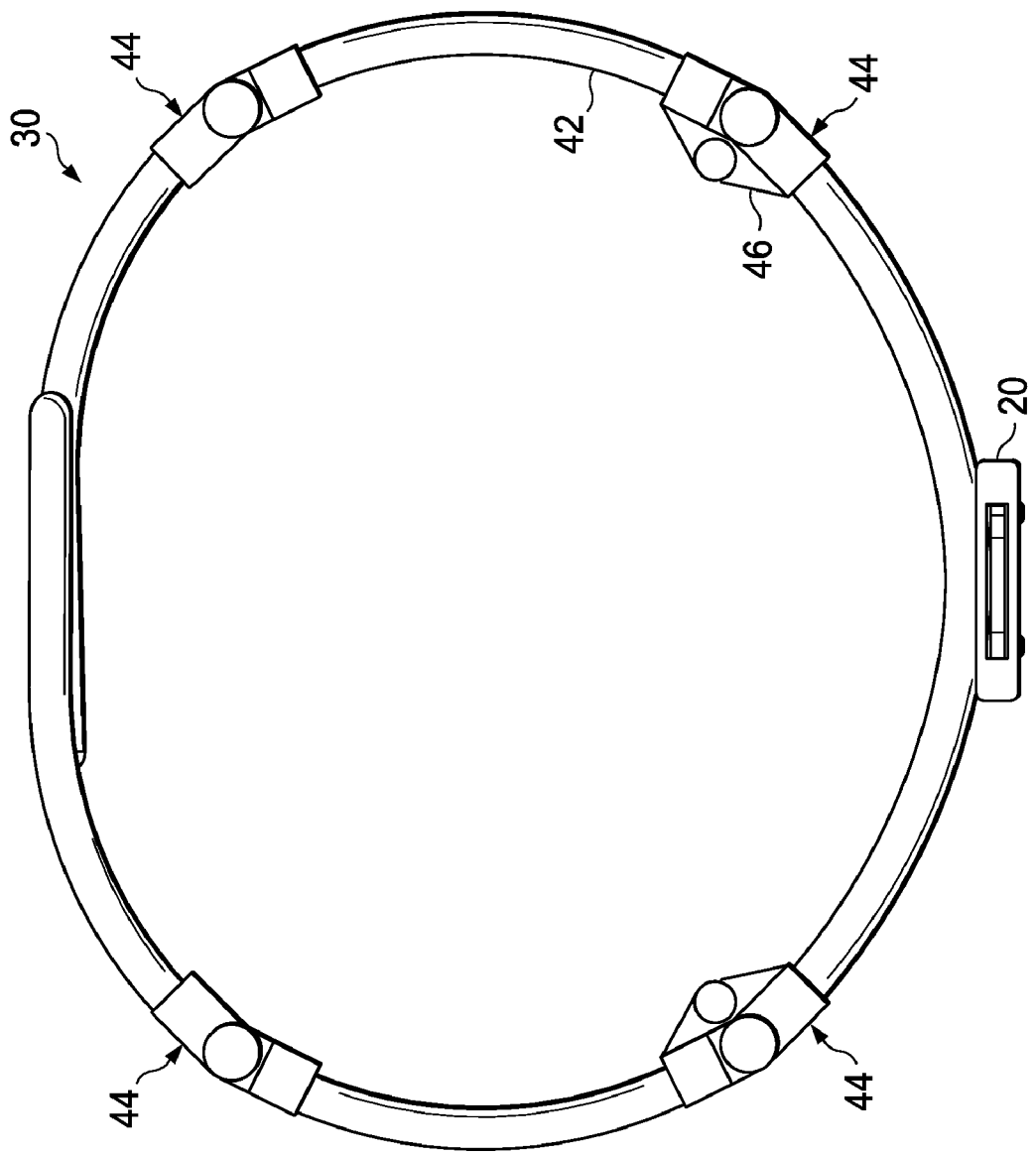
Figure 6C:
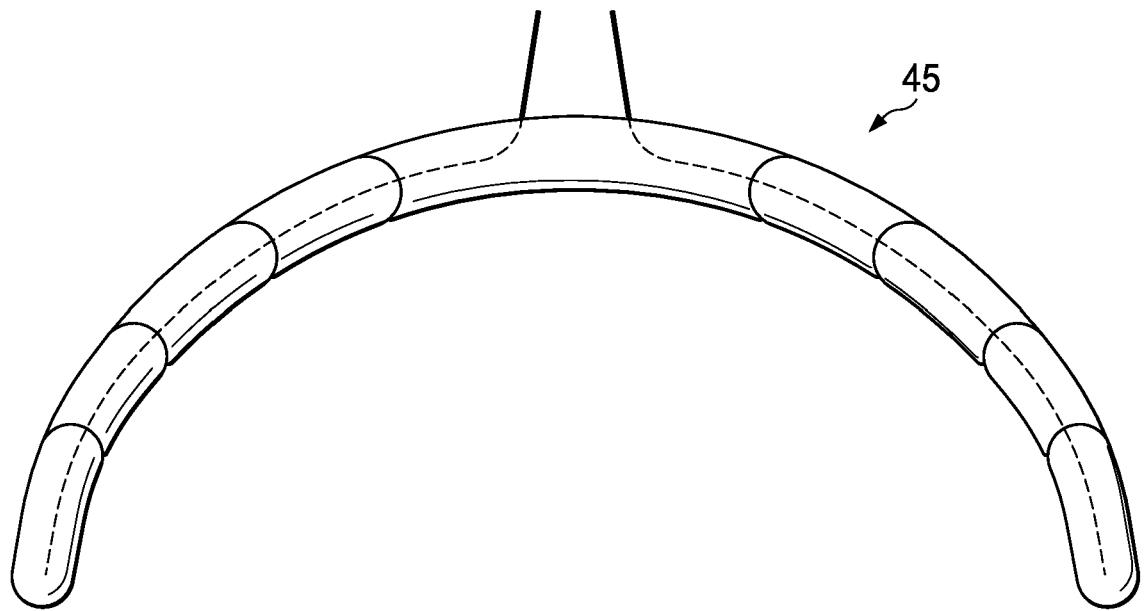
Figure 6D:
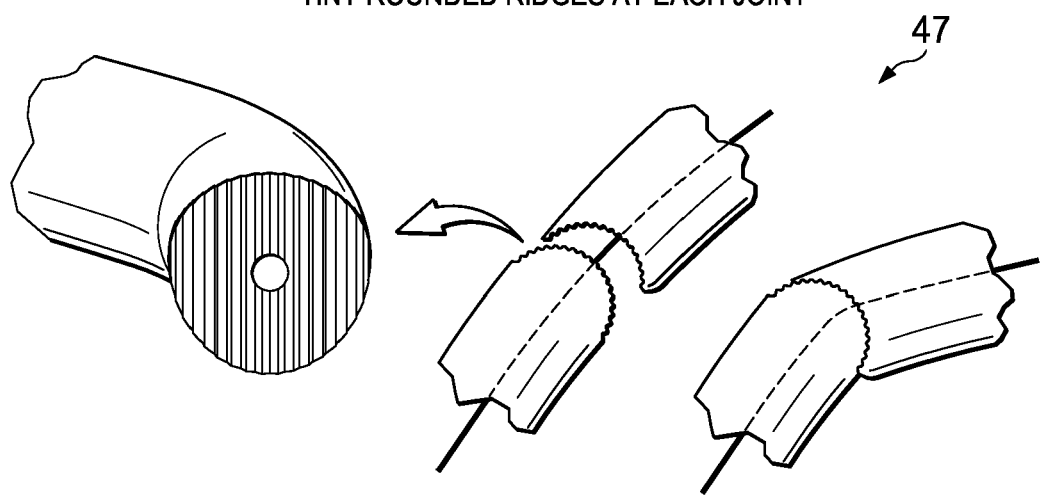

FIGS. 6A-6C illustrate some of the functions of an example belt 30 that includes a quick release 20, a number of flexibility points 42 and 44, and a spring 46, as further detailed by FIG. 6B. The springs are used to keep the hinges in an open position in one example embodiment. FIG. 6C highlights a belt hinge joint mechanism allowing locking or unlocking of many joints simultaneously. A set of cables 45 attach to a tensioner and a quick release mechanism. Tiny rounded ridges 47 are at each joint, whereby a view of the ridges in the joint surface is depicted. In this embodiment, there are many joints with small male ridges and corresponding female depressions on an opposite joint face. These joints may move freely when no tension is on the cable running their length. Upon tensioning the cable, the joints come into forceful contact and the locking ridges prevent hinge motion, and the joints are thereby "locked." When tension is released, the hinges become loose again.

The present invention may be used in conjunction with a corresponding array of hinge joints that provide longitudinal support but no locking mechanism. The underlying "belt" of non-locking joints will support this locking "belt," providing a means of locking and unlocking the joined system of two belts. These two systems may be closely related such that the supporting array contains the ridged-hinge array. Other alternatives could include a single flexible point that allows the belt to open as a set of pinchers. Other variations are certainly within the broad scope of the present invention.

In operation of another example implementation, the lower end of the upper frame component may form an arc around the front of the operator (preferably at, or slightly under, the level of the chin) and pass from one shoulder to the other. This will be in a position to allow a full range of motion of the head. This frame portion can serve as a support system for the lower frame components and everything else below this level, as well as the optically transparent face and head shield, which may rest on this arc or be fixed to it. The face shield may form an arc resembling the frame arc and sweep around the operator's face, possibly with a predominance to the left since that is the side most often exposed to radiation in most settings. Shielding would also be frontal, and the right side (in one example) may be incompletely shielded, although this configuration could easily be altered. Shielding material may also be draped over the shoulder, or supported over the shoulder in a manner like an umbrella in a flexible or rigid manner. Shielding may also be draped over the front of sides of the operator from this top frame component.

The lower portion of the frame may be fixed to the upper portion by three or more attachment pieces (such as rods). This may be rigid, adjustable, or have some flexibility or motion in some directions to allow for different body shapes. The joints may allow expansion or motion within a defined range (possibly only in certain directions) while maintaining rigid support of the desired structures such as the lower frame and radio-protective fabric or shielding material.

Figure 4:
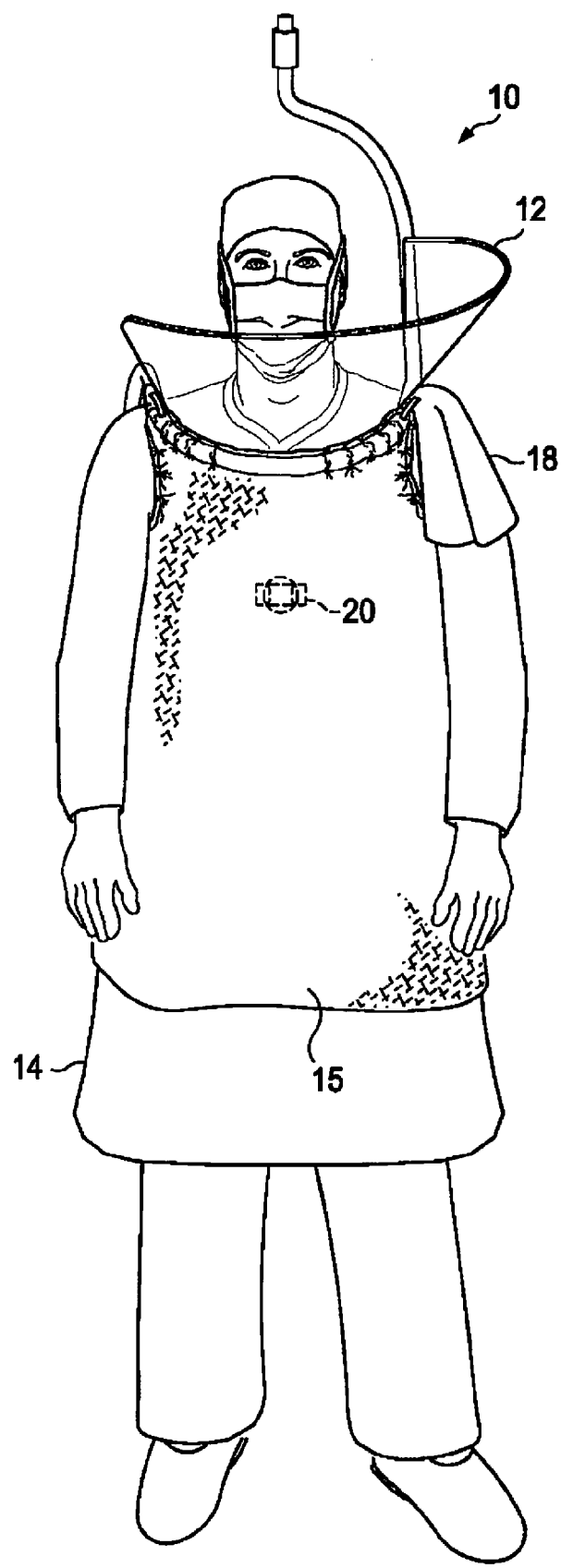
FIG. 4 is a simplified block diagram that illustrates a front view of the personal radiation protective garment in accordance with a particular embodiment of the present invention.

As depicted in FIG. 4, a sterile covering 15 of fabric, paper, or plastic may be shaped to cover the device portions, which will be located at (or below) the chest level of the operator. This can be applied to the device prior to or after engagement of the operator with the device. A possible design of the sterile cover 15 is similar to a large plastic bag, which is passed from the bottom of the shield to the shoulder level by an assistant who does not need to touch the sterile portions, or who wears sterile gloves when applying the bag. This bag will completely contain the device components and allow operation of the belt by allowing the operator to grab the necessary components underneath the sterile layer, much as is common practice currently with sterile ultrasound covers and tableside control panel covers in the catheterization suites.

The sterile cover 15 may be contained within an outer bag that is sterile on the inside (contact with sterile cover) but not necessarily sterile on its outside. This permits it to touch the floor or nearby non-sterile areas as the cover is pulled up over the shield. The outer cover is then stripped off. In another embodiment, the sterile cover 15 is applied by wrapping it around the shield in a horizontal manner [much as one might wrap a towel around their body after swimming] and then securing it with tape, a clamp, or other means.

The sterile cover 15 serves to maintain sterility of the operator. The operator is sterily gowned upon entry into the device. The front of the operator comes into contact with the rear of the shield, which is sterily wrapped in the covering described above. In one operational example, the arms of the operator are held out laterally upon entry, thus not touching anything. The upper part of the shoulder (near the neck) may come into contact with non-sterile components, but this is out of the sterile field and this does not disrupt the sterile field. When the operator approaches the operating table while engaged in the device, the shield that is in front of him is sterile in the same manner that the operator's front would normally be sterile if not using the device. When the operator exits the device, she steps backward and portions of her body that are considered sterile do not brush against the non-sterile portions so the operator remains sterile much as she would be conventionally without the device. Upon re-entry, the rear of the device and the front of the operator have both remained sterile so re-entry does not result in a loss of sterility relative to the initial entry.

The lower portion of the device may contain a structure for supporting the shielding material below the level of the operator's neck. It may be integrated with (or separate from) another frame structure which partially or completely surrounds the operator in a manner similar to a belt [in order to cause the device to remain in close proximity to the operator while he/she moves or walks]. The shielding material may be suspended from the arc-shaped component, which resists downward bending or sagging, thus supporting the shielding material. It may be capable of motion in a plane parallel to the floor to allow wrapping of itself, as well as the shielding material around the operator (either fully or partially). Either integrated with the frame, or separate from the frame, is a belt, which functions similarly to a large clamp that may partially (or completely) surround the operator and which may be operable by the operator without supplemental assistance. Hinges or other flexible components allow the belt to wrap around the operator and to be secured in position by tightening of the hinges and/or closing of the joints with a cable mechanism.

This can include a ratchet or non-ratcheted handle system that pulls the cable with a mechanical advantage so as to close the arms of the belt and secure it around the operator. [Note that many of these possible configurations are outlined in subsequent FIGURES, but a brief description is provided here.] Instead of a cable, a simple hydraulic system may be used for the system. This allows close proximity of the device to the operator for good function upon operator motion. Another mechanism would utilize a partially flexible piece, which when pushed outward or expanded, applies pressure to the belt (thus tightening it around the operator). Another embodiment could utilize a magnetic attachment in the back to allow the rear components to lock together, thus permitting closure of a full circuit around the operator, which could then be tightened by any other manner (possibly as could occur with a conventional belt). Upon sterile exit, the operator could activate a mechanical linkage to the locked magnetic components in the rear using his sterile hands in the front in such a manner so as to unlink the rear components and allow a sterile exit from the device.

In another example, the operator could wear a simple fabric or plastic belt around his chest or waist, with a conventional buckle or hook and loop closure mechanism, which contains a magnet within it. The operator could apply the belt prior to donning the sterile gown or going near the device. It would wrap around her non-sterile shirt. After applying the sterile gown and entering the device, a second magnet in the device would come in close proximity, separated only by the sterile gown and sterile wrappings, with the magnet affixed to the operator. This would result in a magnetic attachment of the device to the operator, such that the device will move with the operator.

This could eliminate the need for an articulated or hinged clamp-like belt that wraps around the operator to keep the device in proximity to the operator. There could be several magnets in the belt and the device to provide a good bond. Or there could be magnets in the device and ferromagnetic material such as steel in the belt, or vice versa. Disengagement could involve a sliding or peeling motion of the operator relative to the device, such as with stooping. Or the operator could grip the frame in the front to help pull it away from the body and other magnet on the operator, until the distance between them is enough to result in sufficient weakening of the attraction so as to result in simple separation.

This distance should not be great since the force is inversely proportional to the square of the distance between the magnets, and the distance between them is minute when they are engaged, so powerful magnets need not be used. Alternatively, electromagnets may be employed in the device, and the belt need only contain ferromagnetic material such as steel. These magnets could be turned on and off as needed to engage/disengage the device.

Another embodiment could utilize slidable components that can be slid backwards to complete a fuller arc around the operator to provide an adequate grip for good function. These would slide rearward on a frame that is otherwise incomplete, which would allow entry of the operator into the system before the slidable components wrapped around their back. In another embodiment, a flexible belt would be suspended in a manner that allowed the operator to enter the device from the rear without becoming contaminated by the belt (either because it was sterile, or because it was suspended over the head for entry, and then dropped down to the chest or abdominal level for securing in the front). Upon sterile exit, the operator would activate a component, which raised the belt high enough for the operator to exit without contamination of the sterile field. Since the belt had been wrapped around the operator, the rear component would be considered non-sterile. Upon re-entry, the operator would enter below the suspended belt and then activate the mechanism, which lowered the belt into proper position for tightening. During this process, an operator could pass his/her arms over the sterile component of the belt at the sides towards the front. In another embodiment, the belt may be passed through a sterile covering such as a sleeve, which permits sliding of the belt around the operator such that the belt remains sterile along its entire length, even though the outer portion of the sleeve is not considered sterile in the rear of the operator.

The frame may permit greater freedom of motion than other configurations, which are shoulder-supported or shoulder-based with regard to main attachment sites of load below the level of the head. Most aprons cross over the shoulders to be supported, which prevents rapid entry and exit while maintaining sterility. If the apron is supported by an overhead support system that has the material draped over the shoulder, there can be some limitation of arm motion, as well as difficulties with rapid exit and re-entry while remaining in proper sterile form, as is considered standard for operative procedures. This new design overcomes those issues, as it permits rapid entry and exit while remaining properly sterile.

FIGS. 7A-7D illustrate quick releases without swivels, as depicted by items 50, 52, and 54. This mechanism can be incorporated into the vertical component of the rigid hanger, which supports the device frame and other components, and is supported by the wire rope or other suspension apparatus that attaches to the top of the arced portion of the hanger. This may be used in particular in combination with a hanger configuration that includes two rigid vertical rod-like components, on both sides of the head, instead of just two uni-lateral component. FIGS. 7E-7I illustrate a number of clutch plate joints and assemblies which may be incorporated into the belt mechanism to facilitate opening and closing including desirable functions of ease of operation, economy of hand motion and maintenance of sterility of hands, and locking function of the belt in the closed configuration so as to keep the frame in proximity to the body during operations. FIG. 7E shows a clutch plate joint 53 that includes a hydraulic extender, a clutch plate, an extension spring, and a pivot pin. In this example, ridges are provided on the plate surfaces. The end-on view of a clutch plate 55 similarly shows a hydraulic extender and an extension spring. A clutch plate 57 is also provided and it offers an angled and a straight configuration, where there are ridges and depressions present. The clutch plate mechanism consists of a joint allowing rotation around a pivot pin. The joint surfaces have rounded male ridges in a radial pattern with corresponding female depressions on the opposite joint surface. When the two clutch plate surfaces are pressed together, the ridges and depressions, in addition to normal friction, result in locking of the two surfaces, thus, locking the joint in its configuration or angle. This is accomplished by the hydraulic extender positioned over one of the surfaces, pushing against it and the outer casing. The casing is fixed, so the clutch plate is pushed against the opposing clutch plate, causing them to lock. When quick release of the lock is desired, the hydraulic pressure is released and the clutch plates may move again, allowing rotation and angulations of the joint.

This is facilitated by extension springs on the opposite side, which push against the casing, pushing the plates apart and allowing free rotation and angulations of the joints. The casing contains the clutch joints, provides longitudinal rigidity to the entire apparatus, and has joints sharing the same pivot pins with the clutch joints (permitting free angulation with the clutch plate joints).

Figure 7A:
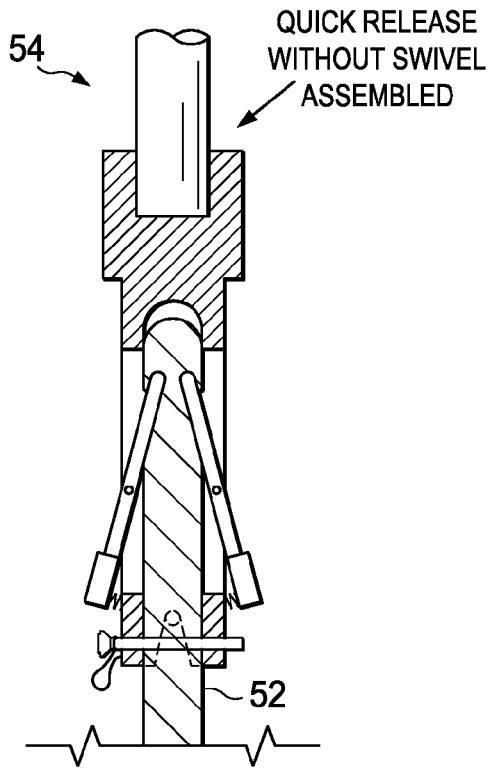
Figure 7B:
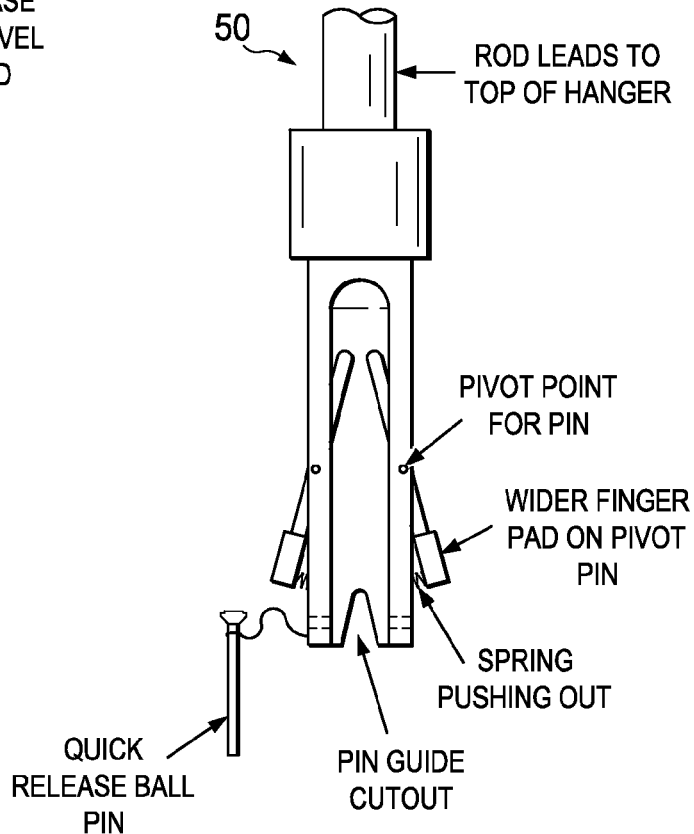
Figure 7C:
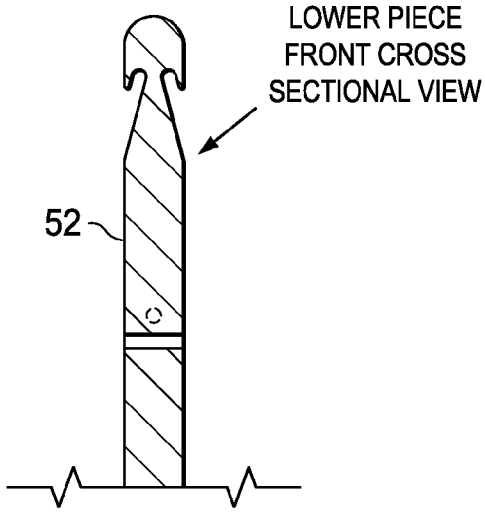
Figure 7D:
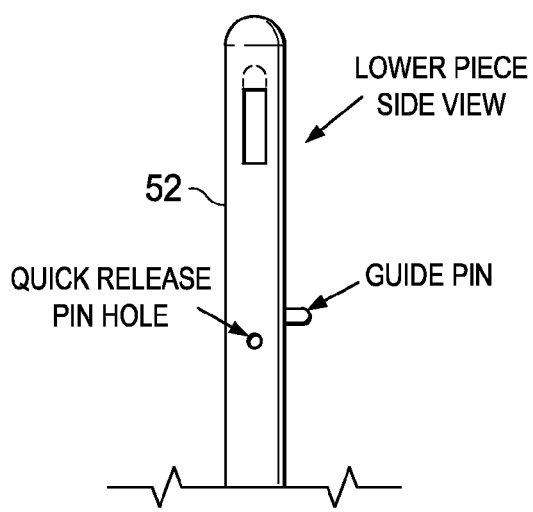
Figure 7H:
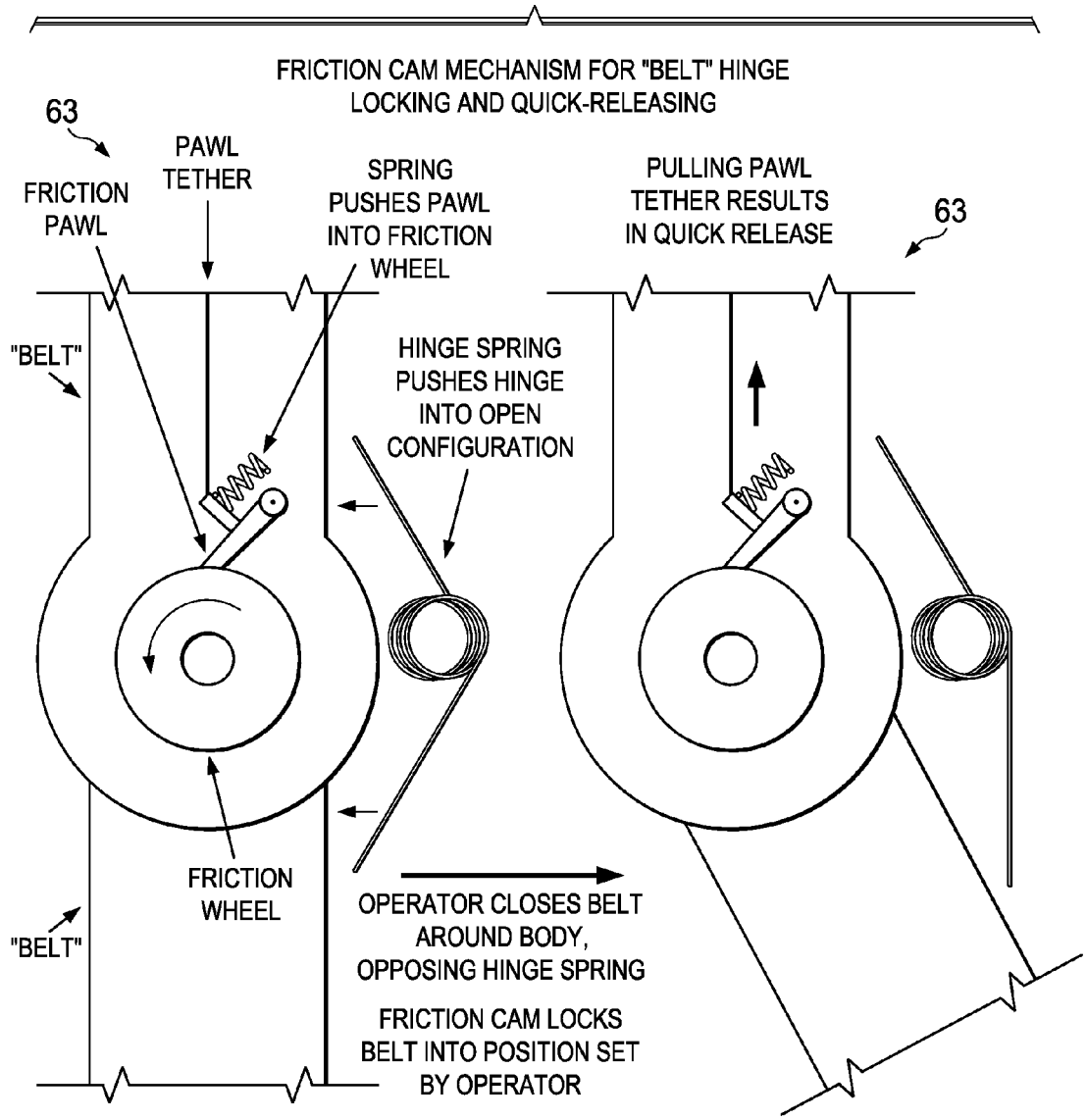
Figure 7I:
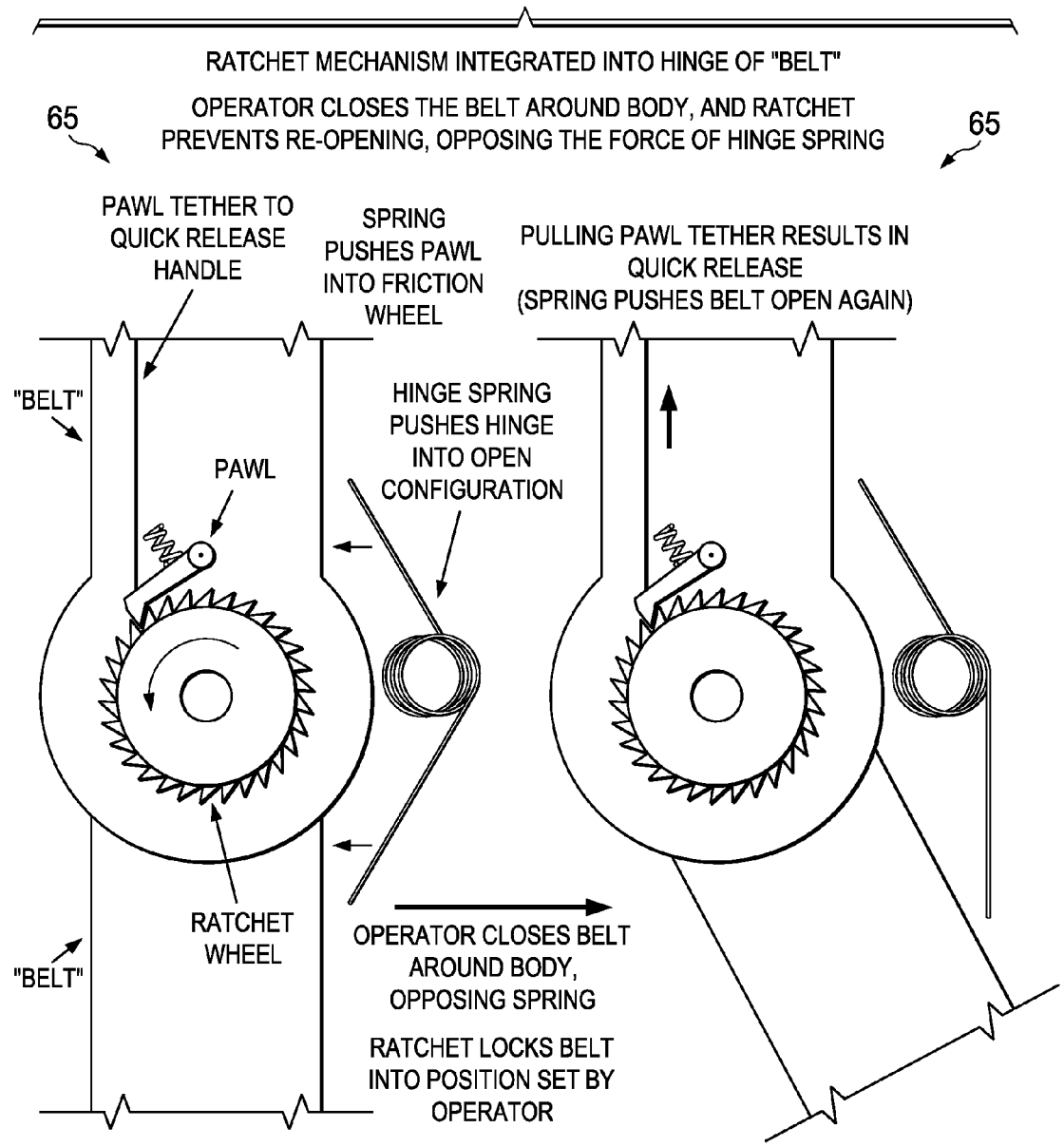

FIG. 7F illustrates a pin lock mechanism 59 for the belt of the garment. FIG. 7G illustrates a ratchet mechanism 61 for the belt of the garment. FIG. 7H illustrates a friction cam mechanism 63 for the belt hinge locking and quick-releasing component. FIG. 7I illustrates a ratchet mechanism 65 to be used with the garment. For purposes of teaching, each of these FIGURES include some directions or guidance for how each component functions. Other ratchet mechanisms of different designs, as in common ratchet wrenches, may also be incorporated.

Figure 8A:
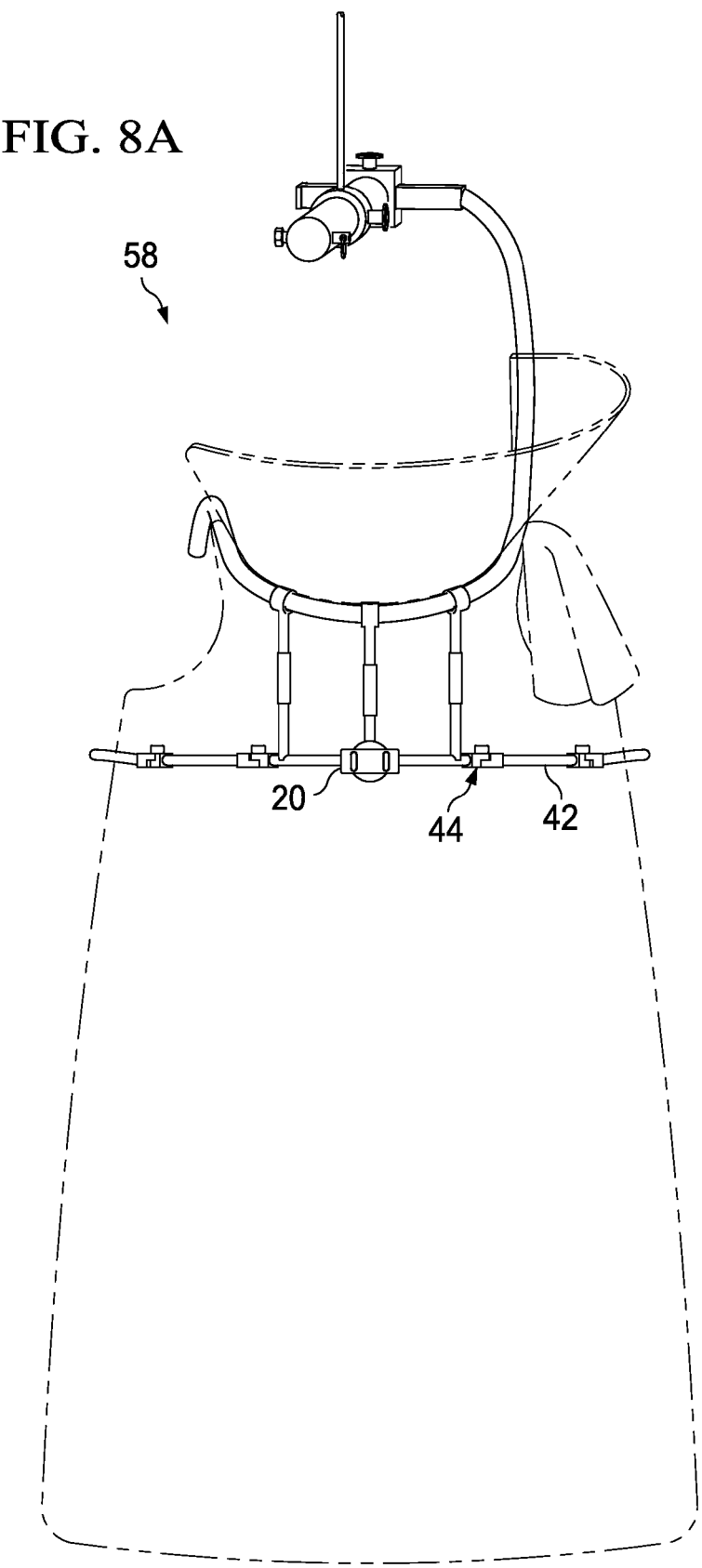
FIGS. 8A-8C are simplified block diagrams that illustrate example frame components of the personal radiation protective garment in accordance with embodiments of the present invention.
Figure 8B:
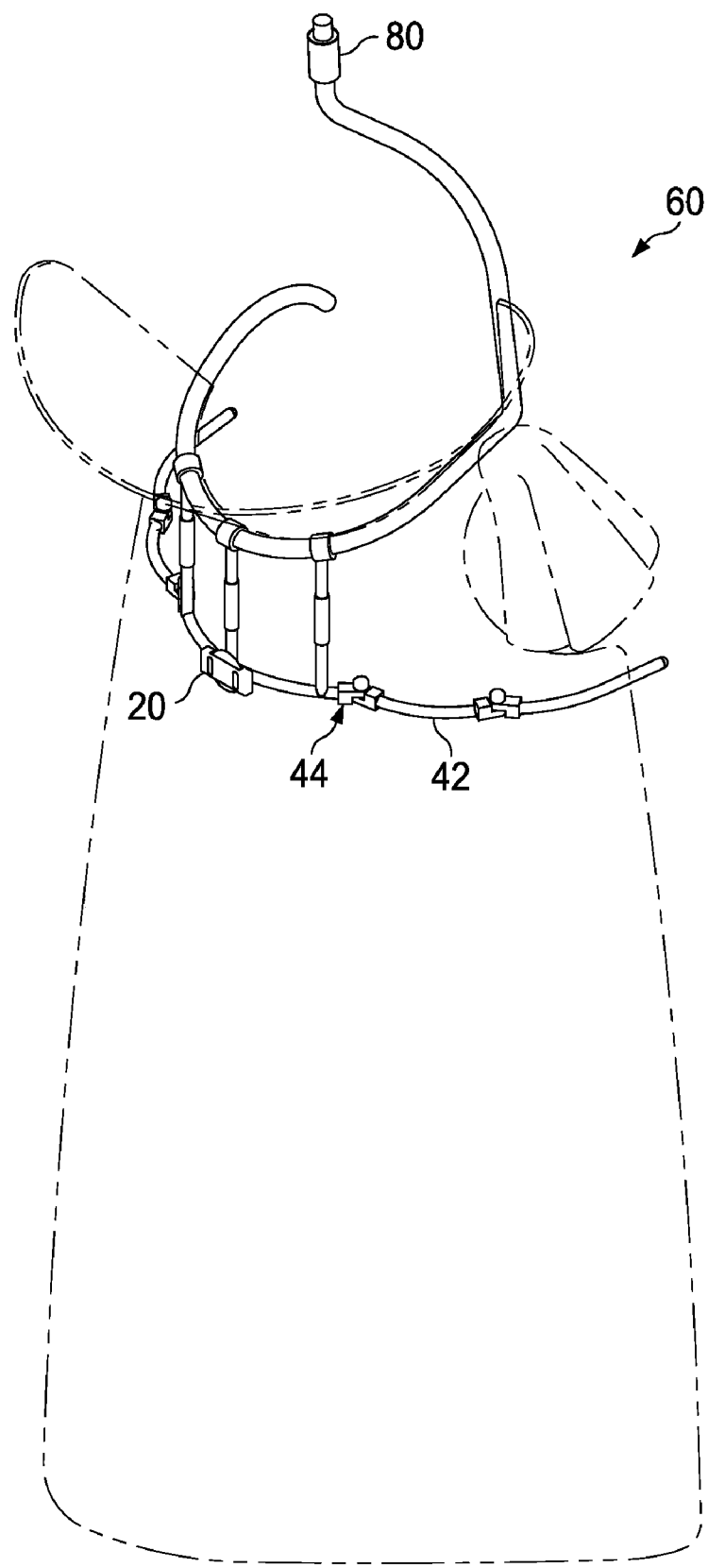
Figure 8C:
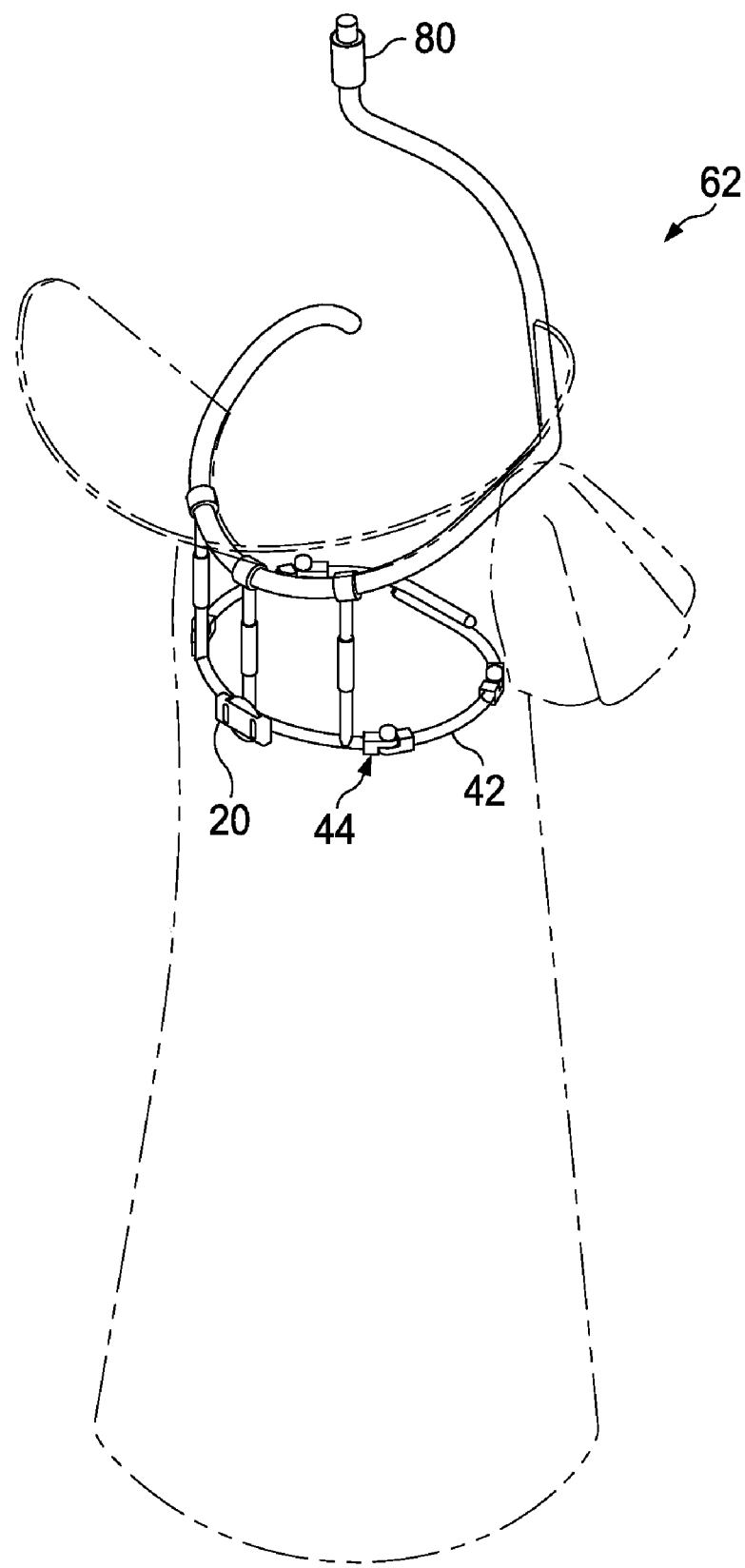
Figure 9:
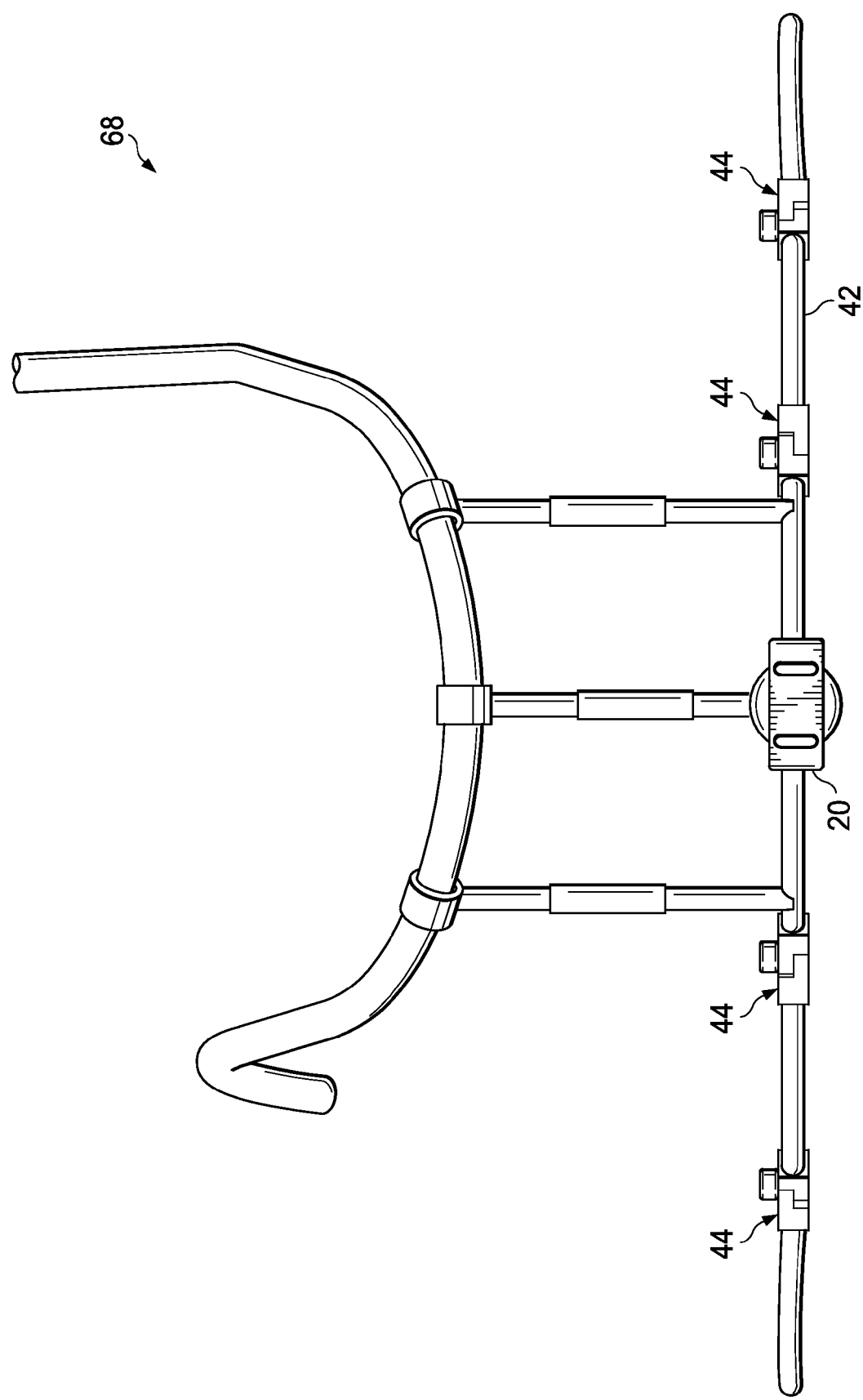
FIG. 9 is a simplified block diagram that illustrates an example garment frame in accordance with an embodiment of the present invention.
Figure 10A:
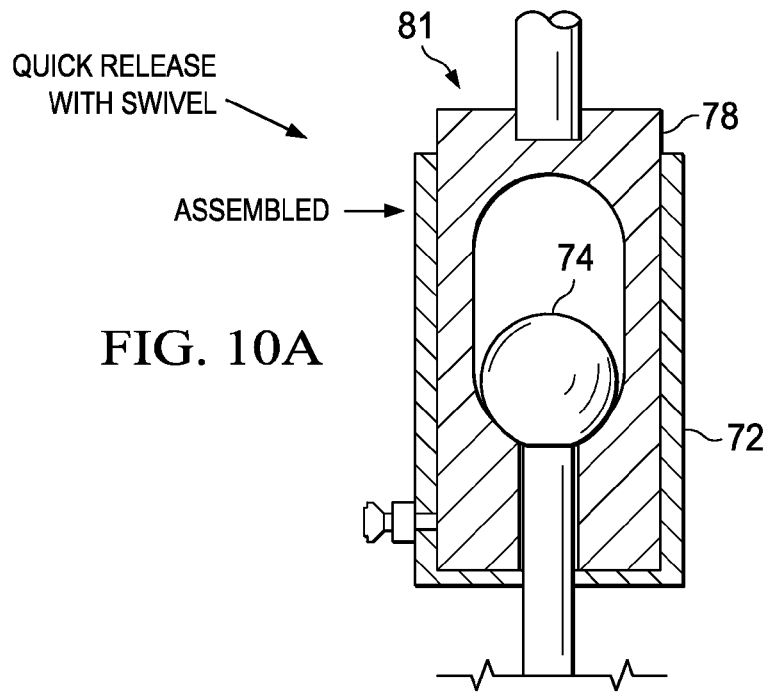
FIGS. 10A-10E are simplified block diagrams that illustrate additional examples of locking components of the personal radiation protective garment in accordance with embodiments of the present invention.
Figure 10B:
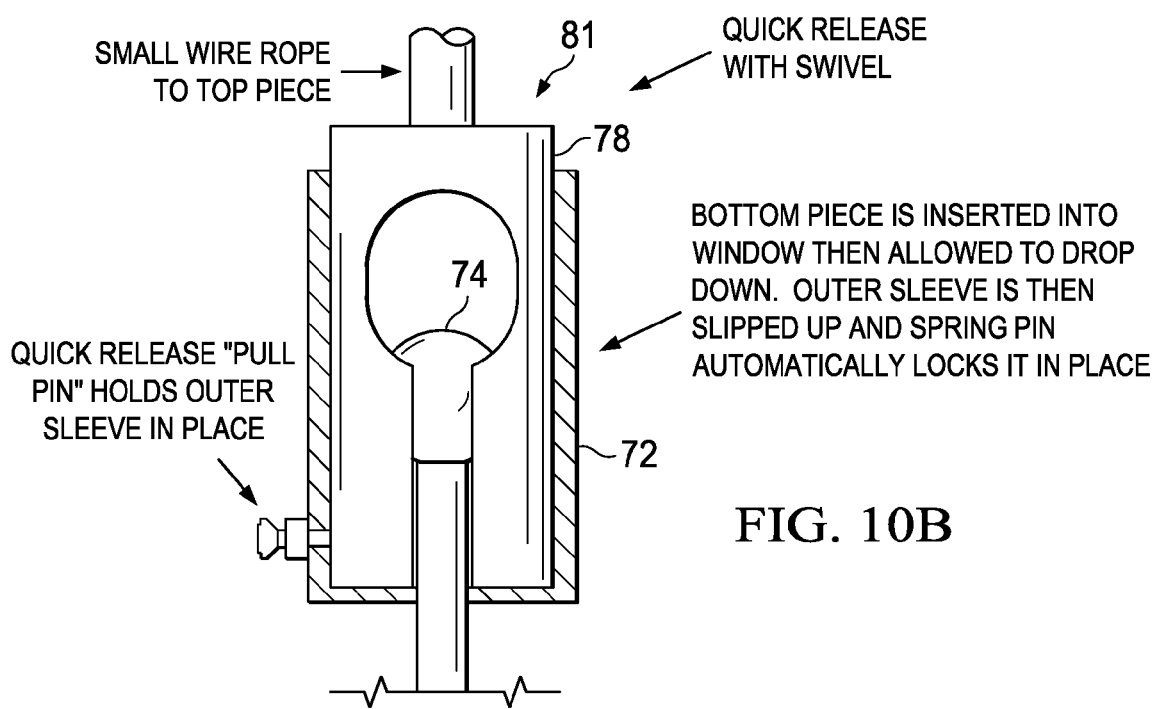
Figure 10C:
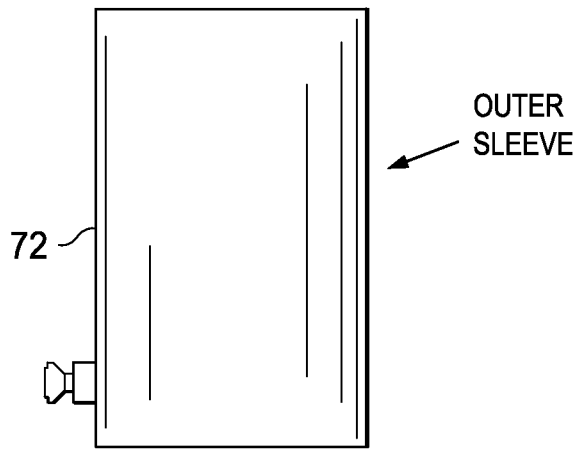
Figure 10D:
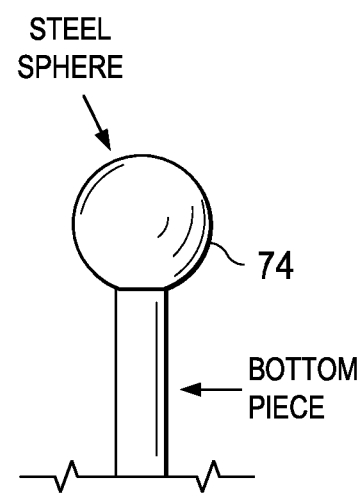
Figure 10E:
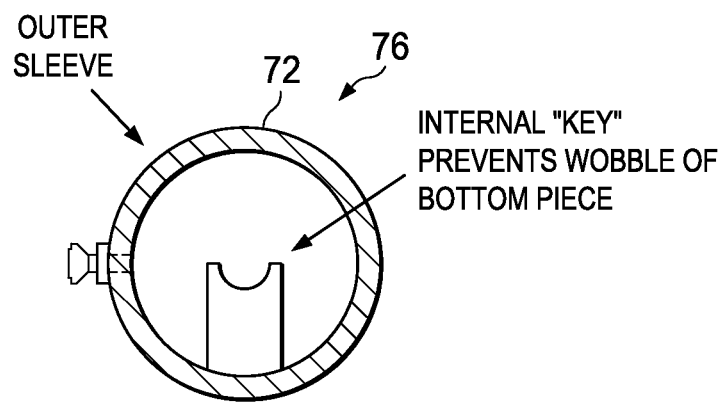

FIGS. 8A-8C illustrate an example design 58 of the garment being described herein. A fastening or securing element 80 is provided with the garment and the frame is provided with release 20 and some flexible belt members 42 and 44. FIG. 8B illustrates another example design 60 and FIG. 8C illustrates yet another example design 62. FIG. 9 illustrates an example of a frame 68 to be used in conjunction with the garment. FIGS. 10A-10E illustrate a number of quick release mechanism examples with accompanying swivels in some cases. These embodiments depict an example configuration 81 that includes a ball component 74 with two casings 72 and 78. FIG. 10E depicts a separate side view 76 that offers another perspective of casing 72.

To better inform the audience, some discussion of the techniques to be used with some of these components is offered. In operation of a typical scenario, an operator or assistant may pre-adjust settings on the garment to make it fit to his/her body shape optimally. This may involve setting the adjustable rigid hinge in the rear, or the connections between the upper and lower frame portions. The balance of the device may also be adjusted by adjusting the cable attachment position on the top of the hanger using the hanger adjustor mechanism, which may then be locked into a preferred position.

An operator or assistant may apply a sterile covering to the device. This may cover device components extending from the bottom of the shield to the level of approximately the mid chest or higher. An operator may perform a surgical scrub of their hands and arms in the usual manner, and then don the surgical sterile gown. The operator may then hold his/her arms up partially and step into the device from the rear and apply the front of his/her body to the rear of the device: lowering the arms in a manner that causes the jointed belt component to close around the operator's body.

In some embodiments, especially in those employing a cable mechanism to retract the belt components, the operator may then activate the tensioner component, which provides sufficient tension to enable a secure closure of the jointed belt around the operator. In other embodiments, such as those employing a ratchet or friction-lock mechanism in the belt, a tensioner is not employed. Tension, or locking, is automatically maintained until the operator chooses to release it for exit. An operator may then perform the normal procedures for treatment of a patient or an animal, or perform other functions that can result in radiation exposure to operators. When an operator desires to become dissociated from the device, he/she may activate the release mechanism, releasing tension on the belt and allowing it to open sufficiently for the purpose of operator exit.

For an exit, the operator lifts their arms partially and steps backwards, dissociating from the device. In one embodiment, the operator will attach a small hook or other attachment component located on the device to a stationary component in the work area, prior to operator dissociation form the device. This may be within the sterile covering and attached to the sterile area (such as the instrument table or the operating table), or it may be outside of the sterile portion of the device (above the shoulder level), and attached to a non-sterile object. This attachment will prevent unwanted motion of the device along the support system, such as crane rails or a trolley, while unattended by the operator, and this will help insure the sterility of sterile components. In other embodiments, a magnet may be used for this purpose instead of a hook.

Re-entry is possible in same manner as the initial entry described above. It is noteworthy and important that the operator can fully operate this device without outside or additional assistance, and while preparing for surgery, and without moving his/her hands anywhere outside the sterile field (such as towards their back, above their upper chest, or below their waist).

Note, as outlined above, there are many configurations disclosed for opening and closing the belt around the operator, locking it in proper position, providing quick release mechanisms for opening the belt, and allowing operator exit. The main goals of these mechanisms are: rapid, easy closure of the belt around the operator, which is usually accomplished by manually squeezing the belt itself with the operator's arms (or alternatively by activating a linkage mechanism utilizing cables, hydraulics, or rigid rod) and closing it at its hinges and mobile joints. Similarly, the device offers a rapid, easy opening of the belt to allow an exit of the operator such that the operator only touches components on (or near) the front of the device without losing sterility. Any required motions of the hands toward the rear area would result in a loss of sterility of the hands. The release mechanisms afford simple gross hand and finger movements so that they can be accomplished through the sterile cover without fumbling.

One important objective in the mechanisms outlined herein is to simply reduce the number of steps to accomplish the sterile entry/exit operations identified above. Yet another objective is automation for the opening of the belt such that the operator only activates a quick release and the other motions are set in motion. This is most simply accomplished by a spring mechanism (wire or gas springs) or a similar tensioning mechanism: exerting forces on the belt or connected apparatus, which results in opening the device. In other embodiments, automation is not incorporated and the belt is opened manually by the operator who either pulls the belt open with her hands, or activates a linkage mechanism that opens the belt.

There are other mechanisms that do not necessarily satisfy all points outlined above, but are still feasible. They may accomplish all necessary actions, but not necessarily with the same expedience, economy of operator involvement, or automation. These mechanisms are also depicted in the FIGURES and discussed herein because they offer viable alternatives and promote some advantages in terms of simplicity or economy of design. In other scenarios, these alternatives are less bulky and/or provide better durability characteristics for the accompanying mechanisms.

FIGS. 11A-11C illustrate grip locks shown on the belt of the garment. For an example design 86 of FIG. 11A, all of the above points identified above are satisfied, where there are no cables. Instead, example design 86 uses metallic rods attached to the belt via articulating (hinge) joints (in some ways similar to the apparatus that is sometimes present on bus doors). Opening the belt to exit the garment requires activation of the quick release only and the closing/locking operation requires manual closing of the belt only. The grip lock mechanism may be in a separate "box" as shown, or integrated into the belt frame as depicted. A front view example design 88 is also provided.

In this instance, the belt is pulled by springs (e.g., flexion springs) at the hinge joints. This is allowed by a quick release, which allows rods to move freely outwards. This allows the hinge to open fully. To close the belt, the operator swings the sides of the belt inwards, pulling the rods outwards. The grip plates lock the rods in place: maintaining the belt in a closed position. Different embodiments allow the spring to attach to the metal rod. This provides more force from the same spring and results in a greater spring excursion. A gripper cage can be swivel-mounted to accommodate the change of angle of the metal rod with motion.

The grip lock mechanism may be attached to the front or the back of the belt at the attachment site beyond the belt hinge joint. This determines if pulling the rods results in opening or closing of the belt. In the depicted version, the springs in front of the belt hinge joints provide the force to open the belt automatically upon release of the grip locks. This spring force could be attached in other locations in other embodiments. For example, it could be attached to the free ends of each metal rod, pulling it outward, or in other ways such as a hinge spring, as seen in FIG. 6B.

In the grip lock example 92 of FIG. 11B, the belt is pulled open by the springs at the hinge joints. This is allowed by a quick release mechanism, which allows rods to move freely inwards. This allows the hinge to open fully. To close the belt, the operator swings the sides of the belt inwards: pulling the rods outwards. The grip plates lock the rods in place: maintaining the belt in the closed position. In another example design 96 of FIG. 11C, long metal rods pass through a casing and through slots in gripping plates secured to the top of the casing. The slot in the gripping plates is just large enough to accommodate the rods when passing perpendicularly through the slot. In this configuration, the rod can pass freely through the plate and the casing. In the neutral position, the extension spring between the gripping plates pushes them apart, resulting in an oblique orientation relative to the casing and the rods. This, combined with the inward tension on the rods due to the springs in the belt (not shown), results in friction between the gripping plates and the rods, thereby locking the rod in position. In one example, this is the "locked" configuration and is the configuration during operation.

As with all the gripping plate mechanisms in the FIG. 11 series, the rod may freely slide in one direction even when the quick release mechanism is not activated. This occurs because in the neutral position, the gripping plates are pushed into an oblique orientation by the extension spring. Force applied to the rod in one direction will cause further obliquity of the gripping plate, resulting in friction lock, whereas force in the opposite direction will move the gripping plate slightly into a less oblique orientation, resulting in effective enlargement of the slot length and permitting movement of the rod through the gripping plate.

This free motion in one direction is used to allow the operator to easily close the device around himself when desired. Closing the belt moves the rods in the direction that permits free motion without activation of the quick release mechanism. In some embodiments, the gripping mechanism may be configured to grip in both directions, requiring activation of the release mechanism to permit both opening and closing of the belt.

When the operator wishes to open the belt to exit the device, the gripping plates are squeezed together by the fingers, resulting in a quick release of the rods. The spring tension in the belt (not shown) will push the rods apart, allowing the belt to open. The advantage of this embodiment over the one using cables is that the rods are automatically positioned in the neutral position (belt open) because the rods are pushed. This eliminates the need for the operator to slide the rods manually, as in the cable version.

In another embodiment, a rack and pinion arrangement may be incorporated into the linkage mechanism instead of friction gripper. The rack links with the belt in an articulated manner similar to described embodiments, but is controlled by a pinion which is controlled by the operator. The pinion may include a ratchet mechanism that allows its rotation in one direction only, until quick release is activated when freedom of motion in both directions is then allowed. Alternatively, the pinion must be released to rotate in either direction.

In another embodiment, a toothed rod is employed instead of the smooth rods depicted in the FIG. 11 series. Instead of a friction gripper plate, there can be a catch mechanism or pawl that sets in between the teeth in the resting or neutral position due to a spring or gravity. The teeth may be angled to as to allow easy direction of the rod in one direction, as the pawl slides over teeth like a ratchet mechanism, whereas it locks with motion in the other direction. A quick release mechanism may allow free motion in either direction. Alternatively, the teeth may be angled such that the device may be locked to motion in both directions until released.

As can now be fully appreciated, such a radiation protection garment offers obvious advantages to operators who work with radiation. This is due, at least in part, to the suspended nature of the garment and shield, which together protect the operator from harmful radiation. System 10 allows an operator to have a great degree of freedom of motion commonly used during medical and research procedures. Furthermore, an operator can remain sterile while using the garment due to its intelligent design and quick release abilities.

It is important to note that the stages and steps described above illustrate only some of the possible operations that may be executed by, or within, the present system. Some of these stages and/or steps may be deleted or removed where appropriate, or these stages and/or steps may be modified, enhanced, or changed considerably without departing from the scope of the present invention. In addition, a number of these operations have been described as being executed concurrently with, or in parallel to, one or more additional operations. However, the timing of these operations may be altered. The preceding example flows have been offered for purposes of teaching and discussion. Substantial flexibility is provided by the tendered system in that any suitable arrangements, chronologies, configurations, and timing mechanisms may be provided without departing from the broad scope of the present invention. Accordingly, any appropriate structure, component, or device may be included within suspended personal radiation protection system 10 to effectuate the tasks and operations of the elements and activities associated with providing optimal radiation protection.

Although the present invention has been described in detail with reference to particular embodiments, it should be understood that various other changes, substitutions, and alterations may be made hereto without departing from the spirit and scope of the present invention. The illustrated device and operations have only been offered for purposes of example and teaching. Suitable alternatives and substitutions are envisioned and contemplated by the present invention: such alternatives and substitutions being clearly within the broad scope of the proposed solutions. Using analogous reasoning, suitable devices that are conducive to properly supporting the weight of the operator, the garment, and the face shield could readily be used or adopted by system 10. In addition, while the foregoing discussion has focused on medical procedures, any other suitable environment requiring radiation protection may benefit from the compatibility teachings provided herein. Similarly, the term 'operator' should be reasonably construed to not only include a living organism but inanimate objects (e.g., tools or robotics) where radiation exposure presents a problem as well.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. A method for radiation protection, comprising:
providing a garment that substantially contours to an operator's body, wherein the garment is operable to protect a portion of the operator's body from radiation, and wherein the garment is suspended by a curved frame attached to a suspension component that reduces a portion of weight of the garment for the operator, a semi-rigid belt secured to the frame in a substantially horizontal orientation and which provides substantial contour to the garment about a portion of the operator's body, and a release mechanism for manipulating the belt that offers an entry into the garment.

2. The method of claim 1, wherein the release mechanism comprises a quick release that allows the operator to disengage from the garment using a single hand movement.

3. The method of claim 1, wherein the belt opens to allow the operator to enter the garment, and wherein the operator, in entering and exiting the garment, is able to limit his contact to components on or near a front of the garment such that the operator can operate the release mechanism for the garment without losing sterility.

4. The method of claim 1, wherein the release mechanism includes a spring mechanism that exerts a force on the belt.

5. The method of claim 1, wherein the garment allows the operator, who is wearing the garment, to move freely in X, Y, and Z spatial planes, and wherein the garment is substantially weightless to the operator.

6. The method of claim 1, wherein the garment includes a sleeve on at least one side of the garment.

7. The method of claim 1, further comprising a face shield, the face shield being substantially weightless to the operator, and wherein the face shield provides additional radiation protection.

8. The method of claim 1, wherein the suspension component is mounted to a ceiling.

9. The method of claim 1, wherein the suspension component is a selected one of a group of components the group consisting of:
   a) an articulating arm or trolley;
   b) a jib crane;
   c) an articulating bridge crane;
   d) a bridge crane;
   e) a reaction arm or power assisted mechanism;
   f) a spring motor;
   g) a telescopic bridge;
   h) a monorail suspension system; and
   i) balancer.

10. The method of claim 1 further comprising a sterile cover for protecting a substantial portion of the garment.

* * * * *